United States Patent
Hayter et al.

(10) Patent No.: US 10,173,007 B2
(45) Date of Patent: *Jan. 8, 2019

(54) CLOSED LOOP CONTROL SYSTEM WITH SAFETY PARAMETERS AND METHODS

(71) Applicant: Abbott Diabetes Care Inc., Alameda, CA (US)

(72) Inventors: Gary Alan Hayter, Oakland, CA (US); Marc Barry Taub, Mountain View, CA (US); Daniel Milfred Bernstein, El Granada, CA (US); Mark Kent Sloan, Redwood City, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/766,644

(22) Filed: Feb. 13, 2013

(65) Prior Publication Data

US 2013/0218126 A1     Aug. 22, 2013

Related U.S. Application Data

(63) Continuation of application No. 12/202,300, filed on Aug. 31, 2008, now Pat. No. 8,377,031.
(Continued)

(51) Int. Cl.
*A61M 5/172*     (2006.01)
*A61B 5/00*      (2006.01)
(Continued)

(52) U.S. Cl.
CPC ....... *A61M 5/1723* (2013.01); *A61B 5/14532* (2013.01); *A61B 5/4839* (2013.01);
(Continued)

(58) Field of Classification Search
CPC ... A61B 5/7275; A61B 5/7282; A61B 5/7221; G06F 19/3468
(Continued)

(56) References Cited

U.S. PATENT DOCUMENTS 3,581,062 A     5/1971     Aston
3,926,760 A    12/1975     Allen et al.
(Continued)

FOREIGN PATENT DOCUMENTS

AU    2003/259741    2/2004
CA       2495648     2/2004
(Continued)

OTHER PUBLICATIONS

Armour, J. C., et al., "Application of Chronic Intravascular Blood Glucose Sensor in Dogs", *Diabetes*, vol. 39, 1990, pp. 1519-1526.
(Continued)

*Primary Examiner* — Bhisma Mehta
*Assistant Examiner* — Jenna Zhang
(74) *Attorney, Agent, or Firm* — Vorys, Sater, Seymour and Pease LLP

(57) ABSTRACT

Methods, system and devices for monitoring a plurality of parameters associated with a closed loop control operation including continuously monitoring a physiological condition and automatic administration of a medication, detecting an adverse condition associated with the monitored physiological condition or the medication administration deviating from a predetermined safety level of the closed loop control operation, and initiating a non-zero pre-programmed medication delivery rate are provided.

19 Claims, 12 Drawing Sheets

Related U.S. Application Data

(60) Provisional application No. 60/982,117, filed on Oct. 23, 2007.

(51) Int. Cl.
*A61B 5/145* (2006.01)
*A61M 5/168* (2006.01)
*A61B 5/1495* (2006.01)
*G16H 20/17* (2018.01)
*A61M 5/142* (2006.01)

(52) U.S. Cl.
CPC .......... *A61B 5/7221* (2013.01); *A61B 5/7275* (2013.01); *A61B 5/746* (2013.01); *A61M 5/16831* (2013.01); *A61B 5/1495* (2013.01); *A61M 2005/14208* (2013.01); *A61M 2205/8212* (2013.01); *A61M 2230/201* (2013.01); *G16H 20/17* (2018.01)

(58) Field of Classification Search
USPC .......................... 604/65–67, 890.1, 503–505
See application file for complete search history.

(56) References Cited

U.S. PATENT DOCUMENTS

| | | |
|---|---|---|
| 3,949,388 A | 4/1976 | Fuller |
| 3,960,497 A | 6/1976 | Acord et al. |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,431,004 A | 2/1984 | Bessman et al. |
| 4,441,968 A | 4/1984 | Emmer et al. |
| 4,464,170 A | 8/1984 | Clemens |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,847,785 A | 7/1989 | Stephens |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,051,688 A | 9/1991 | Murase et al. |
| 5,055,171 A | 10/1991 | Peck |
| 5,068,536 A | 11/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,135,004 A | 8/1992 | Adams et al. |
| 5,165,407 A | 11/1992 | Wilson et al. |
| 5,202,261 A | 4/1993 | Musho et al. |
| 5,204,264 A | 4/1993 | Kaminer et al. |
| 5,210,778 A | 5/1993 | Massart |
| 5,228,449 A | 7/1993 | Christ et al. |
| 5,231,988 A | 8/1993 | Wernicke et al. |
| 5,246,867 A | 9/1993 | Lakowicz et al. |
| 5,251,126 A | 10/1993 | Kahn et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,284,425 A | 2/1994 | Holtermann et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,408,999 A | 4/1995 | Singh et al. |
| 5,410,326 A | 4/1995 | Goldstein |
| 5,411,647 A | 5/1995 | Johnson et al. |
| 5,425,868 A | 6/1995 | Pedersen |
| 5,429,602 A | 7/1995 | Hauser |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,552,997 A | 9/1996 | Massart |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,628,324 A | 5/1997 | Sarbach |
| 5,653,239 A | 8/1997 | Pompei et al. |
| 5,660,163 A | 8/1997 | Schulman et al. |
| 5,665,222 A | 9/1997 | Heller et al. |
| 5,711,001 A | 1/1998 | Bussan et al. |
| 5,711,861 A | 1/1998 | Ward et al. |
| 5,726,646 A | 3/1998 | Bane et al. |
| 5,733,259 A | 3/1998 | Valcke et al. |
| 5,735,285 A | 4/1998 | Albert et al. |
| 5,738,220 A | 4/1998 | Geszler |
| 5,748,103 A | 5/1998 | Flach et al. |
| 5,772,586 A | 6/1998 | Heinonen et al. |
| 5,791,344 A | 8/1998 | Schulman et al. |
| 5,833,603 A | 11/1998 | Kovacs et al. |
| 5,842,189 A | 11/1998 | Keeler et al. |
| 5,899,855 A | 5/1999 | Brown |
| 5,914,026 A | 6/1999 | Blubaugh, Jr. et al. |
| 5,925,021 A | 7/1999 | Castellano et al. |
| 5,935,224 A | 8/1999 | Svancarek et al. |
| 5,942,979 A | 8/1999 | Luppino |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |

(56) References Cited

U.S. PATENT DOCUMENTS

| | | |
|---|---|---|
| 5,980,708 A | 11/1999 | Champagne et al. |
| 5,995,860 A | 11/1999 | Sun et al. |
| 6,001,067 A | 12/1999 | Shults et al. |
| 6,024,699 A | 2/2000 | Surwit et al. |
| 6,028,413 A | 2/2000 | Brockmann |
| 6,049,727 A | 4/2000 | Crothall |
| 6,052,565 A | 4/2000 | Ishikura et al. |
| 6,066,243 A | 5/2000 | Anderson et al. |
| 6,083,710 A | 7/2000 | Heller et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,096,364 A | 8/2000 | Bok et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,143,164 A | 11/2000 | Heller et al. |
| 6,159,147 A | 12/2000 | Lichter et al. |
| 6,162,611 A | 12/2000 | Heller et al. |
| 6,175,752 B1 * | 1/2001 | Say .................. A61B 5/14532 128/903 |
| 6,200,265 B1 | 3/2001 | Walsh et al. |
| 6,212,416 B1 | 4/2001 | Ward et al. |
| 6,219,574 B1 | 4/2001 | Cormier et al. |
| 6,233,471 B1 | 5/2001 | Berner et al. |
| 6,248,067 B1 | 6/2001 | Causey, III et al. |
| 6,254,586 B1 | 7/2001 | Mann et al. |
| 6,270,455 B1 | 8/2001 | Brown |
| 6,275,717 B1 | 8/2001 | Gross et al. |
| 6,283,761 B1 | 9/2001 | Joao |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,299,347 B1 | 10/2001 | Pompei |
| 6,306,104 B1 | 10/2001 | Cunningham et al. |
| 6,309,884 B1 | 10/2001 | Cooper et al. |
| 6,314,317 B1 | 11/2001 | Willis |
| 6,329,161 B1 | 12/2001 | Heller et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,471,689 B1 | 10/2002 | Joseph et al. |
| 6,478,736 B1 | 11/2002 | Mault |
| 6,484,046 B1 | 11/2002 | Say et al. |
| 6,493,069 B1 | 12/2002 | Nagashimada et al. |
| 6,498,043 B1 | 12/2002 | Schulman et al. |
| 6,514,718 B2 | 2/2003 | Heller et al. |
| 6,544,212 B2 | 4/2003 | Galley et al. |
| 6,546,268 B1 | 4/2003 | Ishikawa et al. |
| 6,551,494 B1 | 4/2003 | Heller et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 * | 5/2003 | Steil .................. A61B 5/14532 604/131 |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,545 B2 | 6/2003 | Knobbe et al. |
| 6,574,490 B2 | 6/2003 | Abbink et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,648,821 B2 | 11/2003 | Lebel et al. |
| 6,654,625 B1 | 11/2003 | Say et al. |
| 6,656,114 B1 | 12/2003 | Poulsen et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,733,446 B2 | 5/2004 | Lebel et al. |
| 6,740,075 B2 | 5/2004 | Lebel et al. |
| 6,740,518 B1 | 5/2004 | Duong et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,789,195 B1 | 9/2004 | Prihoda et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,895,263 B2 | 5/2005 | Shin et al. |
| 6,895,265 B2 | 5/2005 | Silver |
| 6,923,763 B1 | 8/2005 | Kovatchev et al. |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman, IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,983,176 B2 | 1/2006 | Gardner et al. |
| 6,990,366 B2 | 1/2006 | Say et al. |
| 6,997,907 B2 | 2/2006 | Safabash et al. |
| 6,998,247 B2 | 2/2006 | Monfre et al. |
| 6,999,854 B2 | 2/2006 | Roth |
| 7,003,336 B2 | 2/2006 | Holker et al. |
| 7,003,340 B2 | 2/2006 | Say et al. |
| 7,003,341 B2 | 2/2006 | Say et al. |
| 7,015,817 B2 | 3/2006 | Copley et al. |
| 7,016,713 B2 | 3/2006 | Gardner et al. |
| 7,022,072 B2 | 4/2006 | Fox et al. |
| 7,022,219 B2 | 4/2006 | Mansouri et al. |
| 7,024,245 B2 | 4/2006 | Lebel et al. |
| 7,025,425 B2 | 4/2006 | Kovatchev et al. |
| 7,027,848 B2 | 4/2006 | Robinson et al. |
| 7,027,931 B1 | 4/2006 | Jones et al. |
| 7,029,444 B2 | 4/2006 | Shin et al. |
| 7,041,068 B2 | 5/2006 | Freeman et al. |
| 7,041,468 B2 | 5/2006 | Drucker et al. |
| 7,046,153 B2 | 5/2006 | Oja et al. |

(56) References Cited

U.S. PATENT DOCUMENTS

| | | |
|---|---|---|
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,092,891 B2 | 8/2006 | Maus et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,134,999 B2 | 11/2006 | Brauker et al. |
| 7,136,689 B2 | 11/2006 | Shults et al. |
| 7,153,265 B2 | 12/2006 | Vachon |
| 7,155,290 B2 | 12/2006 | Von Arx et al. |
| 7,167,818 B2 | 1/2007 | Brown |
| 7,171,274 B2 | 1/2007 | Starkweather et al. |
| 7,174,199 B2 | 2/2007 | Berner et al. |
| 7,179,226 B2 | 2/2007 | Crothall et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,207,974 B2 | 4/2007 | Safabash et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,258,673 B2 | 8/2007 | Racchini et al. |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,286,894 B1 | 10/2007 | Grant et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,402,153 B2 | 7/2008 | Steil et al. |
| 7,404,796 B2 | 7/2008 | Ginsberg |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,474,992 B2 | 1/2009 | Ariyur |
| 7,494,465 B2 | 2/2009 | Brister et al. |
| 7,497,827 B2 | 3/2009 | Brister et al. |
| 7,519,408 B2 | 4/2009 | Rasdal et al. |
| 7,547,281 B2 | 6/2009 | Hayes et al. |
| 7,569,030 B2 | 8/2009 | Lebel et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,651,845 B2 | 1/2010 | Doyle, III et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,699,775 B2 | 4/2010 | Desai et al. |
| 7,699,964 B2 | 4/2010 | Feldman et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,736,310 B2 | 6/2010 | Taub et al. |
| 7,766,829 B2 | 8/2010 | Sloan et al. |
| 7,768,386 B2 | 8/2010 | Hayter et al. |
| 7,768,387 B2 | 8/2010 | Fennell et al. |
| 7,775,444 B2 | 8/2010 | DeRocco et al. |
| 7,778,680 B2 | 8/2010 | Goode et al. |
| 7,811,231 B2 | 10/2010 | Jin et al. |
| 7,813,809 B2 | 10/2010 | Strother et al. |
| 7,826,382 B2 | 11/2010 | Sicurello et al. |
| 7,826,981 B2 | 11/2010 | Goode, Jr. et al. |
| 7,889,069 B2 | 2/2011 | Fifolt et al. |
| 7,899,545 B2 | 3/2011 | John |
| 7,905,833 B2 | 3/2011 | Brister et al. |
| 7,914,450 B2 | 3/2011 | Goode, Jr. et al. |
| 7,920,906 B2 | 4/2011 | Goode et al. |
| 7,928,850 B2 | 4/2011 | Hayter et al. |
| 7,938,797 B2 | 5/2011 | Estes |
| 7,941,200 B2 | 5/2011 | Weinert et al. |
| 7,946,985 B2 | 5/2011 | Mastrototaro et al. |
| 7,972,296 B2 | 7/2011 | Braig et al. |
| 7,976,466 B2 | 7/2011 | Ward et al. |
| 7,978,063 B2 | 7/2011 | Baldus et al. |
| 8,010,174 B2 | 8/2011 | Goode et al. |
| 8,010,256 B2 | 8/2011 | Oowada |
| 8,160,900 B2 | 4/2012 | Taub et al. |
| 8,192,394 B2 | 6/2012 | Estes et al. |
| 8,216,138 B1 | 7/2012 | McGarraugh et al. |
| 8,282,549 B2 | 10/2012 | Brauker et al. |
| 8,461,985 B2 | 6/2013 | Fennell et al. |
| 8,597,570 B2 | 12/2013 | Terashima et al. |
| 2001/0037366 A1 | 11/2001 | Webb et al. |
| 2002/0019022 A1 | 2/2002 | Dunn et al. |
| 2002/0019612 A1 | 2/2002 | Watanabe et al. |
| 2002/0042090 A1 | 4/2002 | Heller et al. |
| 2002/0054320 A1 | 5/2002 | Ogino |
| 2002/0068860 A1 | 6/2002 | Clark |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0128594 A1 | 9/2002 | Das et al. |
| 2002/0147135 A1 | 10/2002 | Schnell |
| 2002/0161288 A1 | 10/2002 | Shin et al. |
| 2002/0169439 A1 | 11/2002 | Flaherty et al. |
| 2002/0169635 A1 | 11/2002 | Shillingburg |
| 2003/0004403 A1 | 1/2003 | Drinan et al. |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0055380 A1 | 3/2003 | Flaherty et al. |
| 2003/0060692 A1 | 3/2003 | Ruchti et al. |
| 2003/0060753 A1* | 3/2003 | Starkweather .... A61M 5/14276 604/66 |
| 2003/0065308 A1 | 4/2003 | Lebel et al. |
| 2003/0100040 A1 | 5/2003 | Bonnecaze et al. |
| 2003/0100821 A1 | 5/2003 | Heller et al. |
| 2003/0114897 A1 | 6/2003 | Von Arx et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0147515 A1 | 8/2003 | Kai et al. |
| 2003/0167035 A1 | 9/2003 | Flaherty et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199790 A1 | 10/2003 | Boecker et al. |
| 2003/0208113 A1 | 11/2003 | Mault et al. |
| 2003/0212317 A1* | 11/2003 | Kovatchev ............. G16H 50/50 600/365 |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2003/0225361 A1 | 12/2003 | Sabra |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0015131 A1 | 1/2004 | Flaherty et al. |
| 2004/0024553 A1 | 2/2004 | Monfre et al. |
| 2004/0034289 A1 | 2/2004 | Teller et al. |

(56) References Cited

U.S. PATENT DOCUMENTS

| | | |
|---|---|---|
| 2004/0039298 A1 | 2/2004 | Abreu |
| 2004/0040840 A1 | 3/2004 | Mao et al. |
| 2004/0041749 A1 | 3/2004 | Dixon |
| 2004/0045879 A1 | 3/2004 | Shults et al. |
| 2004/0054263 A1 | 3/2004 | Moerman et al. |
| 2004/0063435 A1 | 4/2004 | Sakamoto et al. |
| 2004/0064068 A1 | 4/2004 | DeNuzzio et al. |
| 2004/0064088 A1 | 4/2004 | Gorman et al. |
| 2004/0064096 A1 | 4/2004 | Flaherty et al. |
| 2004/0099529 A1 | 5/2004 | Mao et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0133390 A1 | 7/2004 | Osorio et al. |
| 2004/0135684 A1 | 7/2004 | Steinthal et al. |
| 2004/0138588 A1 | 7/2004 | Saikley et al. |
| 2004/0146909 A1 | 7/2004 | Duong et al. |
| 2004/0147872 A1* | 7/2004 | Thompson ............ A61B 5/0028 604/67 |
| 2004/0152622 A1 | 8/2004 | Keith et al. |
| 2004/0153032 A1 | 8/2004 | Garribotto et al. |
| 2004/0167464 A1 | 8/2004 | Ireland et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204687 A1 | 10/2004 | Mogensen et al. |
| 2004/0204868 A1 | 10/2004 | Maynard et al. |
| 2004/0219664 A1 | 11/2004 | Heller et al. |
| 2004/0225338 A1 | 11/2004 | Lebel et al. |
| 2004/0236200 A1 | 11/2004 | Say et al. |
| 2004/0249253 A1 | 12/2004 | Racchini et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0267300 A1 | 12/2004 | Mace |
| 2005/0001024 A1 | 1/2005 | Kusaka et al. |
| 2005/0004439 A1 | 1/2005 | Shin et al. |
| 2005/0004494 A1 | 1/2005 | Perez et al. |
| 2005/0010269 A1 | 1/2005 | Lebel et al. |
| 2005/0017864 A1 | 1/2005 | Tsoukalis |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0070774 A1 | 3/2005 | Addison et al. |
| 2005/0070777 A1 | 3/2005 | Cho et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0096516 A1 | 5/2005 | Soykan et al. |
| 2005/0112169 A1 | 5/2005 | Brauker et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0137530 A1 | 6/2005 | Campbell et al. |
| 2005/0143635 A1 | 6/2005 | Kamath et al. |
| 2005/0154271 A1 | 7/2005 | Rasdal et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187442 A1 | 8/2005 | Cho et al. |
| 2005/0187720 A1 | 8/2005 | Goode, Jr. et al. |
| 2005/0192494 A1 | 9/2005 | Ginsberg |
| 2005/0192557 A1* | 9/2005 | Brauker ............... A61B 5/0002 604/503 |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0214892 A1 | 9/2005 | Kovatchev et al. |
| 2005/0236361 A1 | 10/2005 | Ufer et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0251033 A1 | 11/2005 | Scarantino et al. |
| 2005/0272985 A1 | 12/2005 | Kotulla et al. |
| 2005/0277164 A1 | 12/2005 | Drucker et al. |
| 2005/0277912 A1 | 12/2005 | John |
| 2005/0287620 A1 | 12/2005 | Heller et al. |
| 2006/0001538 A1 | 1/2006 | Kraft et al. |
| 2006/0001551 A1 | 1/2006 | Kraft et al. |
| 2006/0004270 A1 | 1/2006 | Bedard et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0058588 A1 | 3/2006 | Zdeblick |
| 2006/0079740 A1 | 4/2006 | Silver et al. |
| 2006/0091006 A1 | 5/2006 | Wang et al. |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0156796 A1 | 7/2006 | Burke et al. |
| 2006/0166629 A1 | 7/2006 | Reggiardo |
| 2006/0173260 A1 | 8/2006 | Gaoni et al. |
| 2006/0173406 A1* | 8/2006 | Hayes ................ A61B 5/14532 604/67 |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189863 A1 | 8/2006 | Peyser et al. |
| 2006/0193375 A1 | 8/2006 | Lee et al. |
| 2006/0202805 A1 | 9/2006 | Schulman et al. |
| 2006/0211072 A1 | 9/2006 | Ryan et al. |
| 2006/0222566 A1 | 10/2006 | Brauker et al. |
| 2006/0224109 A1 | 10/2006 | Steil et al. |
| 2006/0224141 A1 | 10/2006 | Rush et al. |
| 2006/0229512 A1 | 10/2006 | Petisce et al. |
| 2006/0247508 A1 | 11/2006 | Fennell |
| 2006/0247985 A1 | 11/2006 | Liamos et al. |
| 2006/0253296 A1 | 11/2006 | Liisberg et al. |
| 2006/0258929 A1 | 11/2006 | Goode et al. |
| 2006/0272652 A1 | 12/2006 | Stocker et al. |
| 2006/0281985 A1 | 12/2006 | Ward et al. |

(56) References Cited

U.S. PATENT DOCUMENTS

| | | |
|---|---|---|
| 2006/0290496 A1 | 12/2006 | Peeters et al. |
| 2006/0293607 A1 | 12/2006 | Alt et al. |
| 2007/0007133 A1 | 1/2007 | Mang et al. |
| 2007/0010950 A1 | 1/2007 | Abensour et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0032706 A1 | 2/2007 | Kamath et al. |
| 2007/0032717 A1 | 2/2007 | Brister et al. |
| 2007/0033074 A1 | 2/2007 | Nitzan et al. |
| 2007/0038044 A1 | 2/2007 | Dobbles et al. |
| 2007/0060803 A1 | 3/2007 | Liljeryd et al. |
| 2007/0060814 A1 | 3/2007 | Stafford |
| 2007/0060869 A1 | 3/2007 | Tolle et al. |
| 2007/0060979 A1 | 3/2007 | Strother et al. |
| 2007/0066873 A1 | 3/2007 | Kamath et al. |
| 2007/0066956 A1 | 3/2007 | Finkel |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0078818 A1 | 4/2007 | Zvitz et al. |
| 2007/0093786 A1 | 4/2007 | Goldsmith et al. |
| 2007/0094216 A1 | 4/2007 | Mathias et al. |
| 2007/0100222 A1 | 5/2007 | Mastrototaro et al. |
| 2007/0106135 A1 | 5/2007 | Sloan et al. |
| 2007/0118405 A1 | 5/2007 | Campbell et al. |
| 2007/0124002 A1 | 5/2007 | Estes et al. |
| 2007/0149875 A1 | 6/2007 | Ouyang et al. |
| 2007/0153705 A1 | 7/2007 | Rosar et al. |
| 2007/0156094 A1 | 7/2007 | Safabash et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0191701 A1 | 8/2007 | Feldman et al. |
| 2007/0191702 A1 | 8/2007 | Yodfat et al. |
| 2007/0203407 A1 | 8/2007 | Hoss et al. |
| 2007/0203966 A1 | 8/2007 | Brauker et al. |
| 2007/0208246 A1 | 9/2007 | Brauker et al. |
| 2007/0213657 A1 | 9/2007 | Jennewine et al. |
| 2007/0228071 A1 | 10/2007 | Kamen et al. |
| 2007/0232878 A1 | 10/2007 | Kovatchev et al. |
| 2007/0235331 A1 | 10/2007 | Simpson et al. |
| 2007/0249922 A1 | 10/2007 | Peyser et al. |
| 2007/0255321 A1 | 11/2007 | Gerber et al. |
| 2007/0255348 A1 | 11/2007 | Holtzclaw |
| 2007/0271285 A1 | 11/2007 | Eichorn et al. |
| 2007/0282299 A1 | 12/2007 | Hellwig |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0017522 A1 | 1/2008 | Heller et al. |
| 2008/0021436 A1 | 1/2008 | Wolpert et al. |
| 2008/0021666 A1 | 1/2008 | Goode, Jr. et al. |
| 2008/0029391 A1 | 2/2008 | Mao et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0057484 A1 | 3/2008 | Miyata et al. |
| 2008/0058625 A1 | 3/2008 | McGarraugh et al. |
| 2008/0058626 A1 | 3/2008 | Miyata et al. |
| 2008/0058678 A1 | 3/2008 | Miyata et al. |
| 2008/0058773 A1 | 3/2008 | John |
| 2008/0060955 A1 | 3/2008 | Goodnow |
| 2008/0061961 A1 | 3/2008 | John |
| 2008/0064937 A1 | 3/2008 | McGarraugh et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0097289 A1 | 4/2008 | Steil et al. |
| 2008/0108942 A1 | 5/2008 | Brister et al. |
| 2008/0114228 A1 | 5/2008 | McCluskey et al. |
| 2008/0139910 A1 | 6/2008 | Mastrototaro et al. |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0172205 A1 | 7/2008 | Breton et al. |
| 2008/0177149 A1 | 7/2008 | Weinert et al. |
| 2008/0182537 A1 | 7/2008 | Manku et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0208026 A1 | 8/2008 | Noujaim et al. |
| 2008/0208113 A1 | 8/2008 | Damiano et al. |
| 2008/0214900 A1 | 9/2008 | Fennell et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234663 A1 | 9/2008 | Yodfat et al. |
| 2008/0234943 A1 | 9/2008 | Ray et al. |
| 2008/0242961 A1 | 10/2008 | Brister et al. |
| 2008/0242963 A1 | 10/2008 | Essenpreis et al. |
| 2008/0254544 A1 | 10/2008 | Modzelewski et al. |
| 2008/0255434 A1 | 10/2008 | Hayter et al. |
| 2008/0255437 A1 | 10/2008 | Hayter |
| 2008/0255808 A1 | 10/2008 | Hayter |
| 2008/0256048 A1 | 10/2008 | Hayter |
| 2008/0262469 A1 | 10/2008 | Brister et al. |
| 2008/0269714 A1 | 10/2008 | Mastrototaro et al. |
| 2008/0269723 A1 | 10/2008 | Mastrototaro et al. |
| 2008/0275313 A1 | 11/2008 | Brister et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319085 A1 | 12/2008 | Wright et al. |
| 2008/0319279 A1 | 12/2008 | Ramsay et al. |

(56) References Cited

U.S. PATENT DOCUMENTS

| | | |
|---|---|---|
| 2008/0319295 A1 | 12/2008 | Bernstein et al. |
| 2008/0319296 A1 | 12/2008 | Bernstein et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085873 A1 | 4/2009 | Betts et al. |
| 2009/0088614 A1 | 4/2009 | Taub et al. |
| 2009/0093687 A1 | 4/2009 | Telfort et al. |
| 2009/0099436 A1 | 4/2009 | Brister et al. |
| 2009/0105560 A1 | 4/2009 | Solomon |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0177068 A1 | 7/2009 | Stivoric et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216100 A1 | 8/2009 | Ebner et al. |
| 2009/0216103 A1 | 8/2009 | Brister et al. |
| 2009/0227855 A1 | 9/2009 | Hill et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0240440 A1 | 9/2009 | Shurabura et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247931 A1 | 10/2009 | Damgaard-Sorensen |
| 2009/0253973 A1 | 10/2009 | Bashan et al. |
| 2009/0287073 A1 | 11/2009 | Boock et al. |
| 2009/0287074 A1 | 11/2009 | Shults et al. |
| 2009/0292188 A1 | 11/2009 | Hoss et al. |
| 2009/0296742 A1 | 12/2009 | Sicurello et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0056992 A1 | 3/2010 | Hayter et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0076283 A1 | 3/2010 | Simpson et al. |
| 2010/0081906 A1 | 4/2010 | Hayter et al. |
| 2010/0081908 A1 | 4/2010 | Dobbles et al. |
| 2010/0081909 A1 | 4/2010 | Budiman et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0119693 A1 | 5/2010 | Tapsak et al. |
| 2010/0121169 A1 | 5/2010 | Petisce et al. |
| 2010/0141656 A1 | 6/2010 | Krieftewirth |
| 2010/0152554 A1 | 6/2010 | Steine et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174266 A1 | 7/2010 | Estes |
| 2010/0185175 A1 | 7/2010 | Kamen et al. |
| 2010/0191082 A1 | 7/2010 | Brister et al. |
| 2010/0204557 A1 | 8/2010 | Kiaie et al. |
| 2010/0213080 A1 | 8/2010 | Celentano et al. |
| 2010/0240975 A1 | 9/2010 | Goode et al. |
| 2010/0274111 A1 | 10/2010 | Say et al. |
| 2010/0292634 A1* | 11/2010 | Kircher, Jr. ........ A61B 5/14532 604/66 |
| 2010/0312176 A1 | 12/2010 | Lauer et al. |
| 2010/0313105 A1 | 12/2010 | Nekoomaram et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |

(56) References Cited

U.S. PATENT DOCUMENTS

| | | |
|---|---|---|
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0031986 A1 | 2/2011 | Bhat et al. |
| 2011/0077490 A1 | 3/2011 | Simpson et al. |
| 2011/0148905 A1 | 6/2011 | Simmons et al. |
| 2011/0208027 A1 | 8/2011 | Wagner et al. |
| 2011/0257895 A1 | 10/2011 | Brauker et al. |
| 2011/0287528 A1 | 11/2011 | Fern et al. |
| 2011/0289497 A1 | 11/2011 | Kiaie et al. |
| 2011/0320130 A1 | 12/2011 | Valdes et al. |
| 2012/0078071 A1 | 3/2012 | Bohm et al. |
| 2012/0108934 A1 | 5/2012 | Valdes et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0190989 A1 | 7/2012 | Kaiser et al. |
| 2013/0035575 A1 | 2/2013 | Mayou et al. |
| 2013/0235166 A1 | 9/2013 | Jones et al. |

FOREIGN PATENT DOCUMENTS

| | | |
|---|---|---|
| CA | 2498682 | 9/2005 |
| CA | 2555749 | 9/2005 |
| CA | 2632709 | 6/2007 |
| CA | 2615575 | 6/2008 |
| CA | 2701374 | 4/2009 |
| DE | 4401400 | 7/1995 |
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 1568309 | 8/2005 |
| EP | 1956371 | 8/2008 |
| EP | 2260757 | 12/2010 |
| WO | WO-1993/006237 | 4/1993 |
| WO | WO-1996/025089 | 8/1996 |
| WO | WO-1996/035370 | 11/1996 |
| WO | WO-1998/035053 | 8/1998 |
| WO | WO-1999/056613 | 11/1999 |
| WO | WO-2000/049940 | 8/2000 |
| WO | WO-2000/059370 | 10/2000 |
| WO | WO-2000/074753 | 12/2000 |
| WO | WO-2000/078992 | 12/2000 |
| WO | WO-2001/052935 | 7/2001 |
| WO | WO-2001/054753 | 8/2001 |
| WO | WO-2002/016905 | 2/2002 |
| WO | WO-2002/058537 | 8/2002 |
| WO | WO-2003/076893 | 9/2003 |
| WO | WO-2003/082091 | 10/2003 |
| WO | WO-2003/085372 | 10/2003 |
| WO | WO-2004/015539 | 2/2004 |
| WO | WO-2004/047445 | 6/2004 |
| WO | WO-2004/061420 | 7/2004 |
| WO | WO-2005/010756 | 2/2005 |
| WO | WO-2005/040404 | 5/2005 |
| WO | WO-2005/041766 | 5/2005 |
| WO | WO-2005/089103 | 9/2005 |
| WO | WO-2006/024671 | 3/2006 |
| WO | WO-2006/051466 | 5/2006 |
| WO | WO-2006/064397 | 6/2006 |
| WO | WO-2006/079114 | 7/2006 |
| WO | WO-2006/118947 | 11/2006 |
| WO | WO-2007/007459 | 1/2007 |
| WO | WO-2007/016399 | 2/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/056638 | 5/2007 |
| WO | WO-2007/065285 | 6/2007 |
| WO | WO-2007/097754 | 8/2007 |
| WO | WO-2007/101223 | 9/2007 |
| WO | WO-2007/120363 | 10/2007 |
| WO | WO-2007/126444 | 11/2007 |
| WO | WO-2007/053832 | 12/2007 |
| WO | WO-2007/143225 | 12/2007 |
| WO | WO-2007/149319 | 12/2007 |
| WO | WO-2008/001366 | 1/2008 |
| WO | WO-2008/021913 | 2/2008 |
| WO | WO-2008/042760 | 4/2008 |
| WO | WO-2008/086541 | 7/2008 |
| WO | WO-2008/128210 | 10/2008 |
| WO | WO-2008/130896 | 10/2008 |
| WO | WO-2008/130897 | 10/2008 |
| WO | WO-2008/130898 | 10/2008 |
| WO | WO-2008/143943 | 11/2008 |
| WO | WO-2008/151452 | 12/2008 |
| WO | WO-2009/018058 | 2/2009 |
| WO | WO-2009/049252 | 4/2009 |
| WO | WO-2009/086216 | 7/2009 |
| WO | WO-2009/096992 | 8/2009 |
| WO | WO-2009/097594 | 8/2009 |
| WO | WO-2010/077329 | 7/2010 |
| WO | WO-2011/104616 | 9/2011 |

OTHER PUBLICATIONS

Aussedat, B., et al., "A User-Friendly Method for Calibrating a Subcutaneous Glucose Sensor-Based Hypoglycemic Alarm", *Biosensors & Bioelectronics*, vol. 12, No. 11, 1997, pp. 1061-1070.

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Cheyne, E. H., et al., "Performance of a Continuous Glucose Monitoring System During Controlled Hypoglycaemia in Healthy Volunteers", *Diabetes Technology & Therapeutics*, vol. 4, No. 5, 2002, pp. 607-613.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

El-Khatib, F. H, et al., "Adaptive Closed-Loop Control Provides Blood-Glucose Regulation Using Subcutaneous Insulin and Glucagon Infusion in Diabetic Swine", *Journal of Diabetes Science and Technology*, vol. 1, No. 2, 2007, pp. 181-192.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Garg, S., et al., "Improvement in Glycemic Excursions with a Transcutaneous, Real-Time Continuous Glucose Sensor", *Diabetes Care*, vol. 29, No. 1, 2006, pp. 44-50.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

(56) References Cited

OTHER PUBLICATIONS

Johnson, P. C., "Peripheral Circulation", *John Wiley & Sons*, 1978, pp. 198.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Kuure-Kinsey, M., et al., "A Dual-Rate Kalman Filter for Continuous Glucose Monitoring", *Proceedings of the 28th IEEE, EMBS Annual International Conference*, New York City, 2006, pp. 63-66.

Lo, B., et al., "Key Technical Challenges and Current Implementations of Body Sensor Networks", *Body Sensor Networks*, 2005, pp. 1-5.

Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.

Lortz, J., et al., "What is Bluetooth? We Explain the Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectroscopy", *Clinical Chemistry*, vol. 45, No. 9, 1999, pp. 1651-1658.

McGarraugh, G., et al., "Glucose Measurements Using Blood Extracted from the Forearm and the Finger", *TheraSense, Inc.*, 2001, 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Morbiducci, U, et al., "Improved Usability of the Minimal Model of Insulin Sensitivity Based on an Automated Approach and Genetic Algorithms for Parameter Estimation", *Clinical Science*, vol. 112, 2007, pp. 257-263.

Mougiakakou, et al., "A Real Time Simulation Model of Glucose-Insulin Metabolism for Type 1 Diabetes Patients", *Proceedings of the 2005 IEEE*, 2005, pp. 298-301.

Parker, R., et al., "Robust H∞ Glucose Control in Diabetes Using a Physiological Model", *AIChE Journal*, vol. 46, No. 12, 2000, pp. 2537-2549.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Rodriguez, N., et al., "Flexible Communication and Control Protocol for Injectable Neuromuscular Interfaces", *IEEE Transactions on Biomedical Circuits and Systems*, vol. 1, No. 1, 2007, pp. 19-27.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

PCT Application No. PCT/US2009/055453, International Preliminary Report on Patentability and Written Opinion of the International Searching Authority dated Mar. 10, 2011.

PCT Application No. PCT/US2009/055453, International Search Report and Written Opinion of the International Searching Authority dated Oct. 20, 2009.

PCT Application No. PCT/US2009/055454, International Preliminary Report on Patentability and Written Opinion of the International Searching Authority dated Mar. 10, 2011.

PCT Application No. PCT/US2009/055454, International Search Report and Written Opinion of the International Searching Authority dated Oct. 20, 2009.

PCT Application No. PCT/US2009/055455, International Preliminary Report on Patentability and Written Opinion of the International Searching Authority dated Mar. 10, 2011.

PCT Application No. PCT/US2009/055455, International Search Report and Written Opinion of the International Searching Authority dated Oct. 7, 2009.

(56) References Cited

OTHER PUBLICATIONS

PCT Application No. PCT/US2009/055457, International Preliminary Report on Patentability and Written Opinion of the International Searching Authority dated Mar. 10, 2011.
PCT Application No. PCT/US2009/055457, International Search Report and Written Opinion of the International Searching Authority dated Nov. 13, 2009.
PCT Application No. PCT/US2009/055458, International Preliminary Report on Patentability and Written Opinion of the International Searching Authority dated Mar. 10, 2011.
PCT Application No. PCT/US2009/055458, International Search Report and Written Opinion of the International Searching Authority dated Oct. 7, 2009.
PCT Application No. PCT/US2009/055459, International Preliminary Report on Patentability and Written Opinion of the International Searching Authority dated Mar. 10, 2011.
PCT Application No. PCT/US2009/055459, International Search Report and Written Opinion of the International Searching Authority dated Oct. 22, 2009.
U.S. Appl. No. 12/202,300, Notice of Allowance dated Dec. 20, 2012.
U.S. Appl. No. 12/202,300, Office Action dated Apr. 13, 2012.
U.S. Appl. No. 12/202,300, Office Action dated Aug. 20, 2010.
U.S. Appl. No. 12/202,300, Office Action dated Dec. 23, 2010.
U.S. Appl. No. 12/202,300, Office Action dated Jun. 2, 2010.
U.S. Appl. No. 12/202,300, Office Action dated Nov. 27, 2009.
U.S. Appl. No. 12/202,300, Office Action dated Sep. 14, 2012.
U.S. Appl. No. 12/202,301, Advisory Action dated May 28, 2010.
U.S. Appl. No. 12/202,301, Office Action dated Aug. 12, 2009.
U.S. Appl. No. 12/202,301, Office Action dated Mar. 9, 2010.
U.S. Appl. No. 12/202,302, Office Action dated Apr. 23, 2010.
U.S. Appl. No. 12/202,302, Office Action dated Jul. 9, 2009.
U.S. Appl. No. 12/202,302, Office Action dated May 10, 2013.
U.S. Appl. No. 12/202,302, Office Action dated Nov. 3, 2009.
U.S. Appl. No. 12/202,302, Office Action dated Oct. 18, 2010.
U.S. Appl. No. 12/202,304, Advisory Action dated Apr. 20, 2010.
U.S. Appl. No. 12/202,304, Office Action dated Jan. 11, 2010.
U.S. Appl. No. 12/202,304, Office Action dated Jul. 16, 2009.
U.S. Appl. No. 12/202,304, Office Action dated May 15, 2013.
U.S. Appl. No. 12/202,305, Advisory Action dated May 18, 2010.
U.S. Appl. No. 12/202,305, Office Action dated Apr. 13, 2011.
U.S. Appl. No. 12/202,305, Office Action dated Aug. 2, 2010.
U.S. Appl. No. 12/202,305, Office Action dated Dec. 28, 2009.
U.S. Appl. No. 12/202,305, Office Action dated Jul. 8, 2009.
U.S. Appl. No. 12/202,306, Advisory Action dated Jul. 20, 2010.
U.S. Appl. No. 12/202,306, Advisory Action dated Oct. 1, 2012.
U.S. Appl. No. 12/202,306, Office Action dated Apr. 1, 2011.
U.S. Appl. No. 12/202,306, Office Action dated Dec. 27, 2011.
U.S. Appl. No. 12/202,306, Office Action dated Dec. 8, 2009.
U.S. Appl. No. 12/202,306, Office Action dated Jul. 5, 2012.
U.S. Appl. No. 12/202,306, Office Action dated May 13, 2010.
U.S. Appl. No. 12/580,915, Office Action dated Feb. 1, 2012.
Bremer, T. M., et al., "Benchmark Data from the Literature for Evaluation of New Glucose Sensing Technologies", *Diabetes Technology & Therapeutics*, vol. 3, No. 3, 2001, pp. 409-418.
Panteleon, A. E., et al., "The Role of the Independent Variable to Glucose Sensor Calibration", *Diabetes Technology & Therapeutics*, vol. 5, No. 3, 2003, pp. 401-410.
U.S. Appl. No. 12/202,301, Office Action dated Oct. 23, 2013.
U.S. Appl. No. 12/202,302, Office Action dated Nov. 27, 2013.
U.S. Appl. No. 12/202,304, Office Action dated Dec. 6, 2013.
U.S. Appl. No. 12/202,305, Office Action dated Nov. 6, 2013.
U.S. Appl. No. 12/202,306, Notice of Allowance dated Sep. 5, 2013.
U.S. Appl. No. 12/580,915, Office Action dated Dec. 10, 2013.
Arnold, M. A., et al., "Selectivity Assessment of Noninvasive Glucose Measurements Based on Analysis of Multivariate Calibration Vectors", *Journal of Diabetes Science and Technology*, vol. 1, No. 4, 2007, pp. 454-462.
Eren-Oruklu, M., et al., "Estimation of Future Glucose Concentrations with Subject-Specific Recursive Linear Models", *Diabetes Technology & Therapeutics* vol. 11(4), 2009, pp. 243-253.
Li, Y., et al., "In Vivo Release From a Drug Delivery MEMS Device", *Journal of Controlled Release*, vol. 100, 2004, 99. 211-219.
U.S. Appl. No. 12/202,304, Office Action dated Jul. 15, 2014.
U.S. Appl. No. 12/202,304, Office Action dated Oct. 23, 2014.
U.S. Appl. No. 12/202,305, Notice of Allowance dated Jan. 21, 2014.
U.S. Appl. No. 12/580,915, Advisory Action dated Mar. 7, 2014.
U.S. Appl. No. 12/580,915, Notice of Allowance dated Apr. 14, 2014.

\* cited by examiner

CLOSED LOOP CONTROL SYSTEM WITH SAFETY PARAMETERS AND METHODS

RELATED APPLICATIONS

The present application is a continuation of U.S. patent application Ser. No. 12/202,300 filed Aug. 31, 2008, entitled "Closed Loop Control System with Safety Parameters and Methods", which claims priority under 35 U.S.C. § 119(e) to U.S. provisional application No. 60/982,117 filed Oct. 23, 2007, entitled "Diabetes Management", and assigned to the Assignee of the present application, Abbott Diabetes Care Inc. of Alameda, Calif., the disclosures of each of which are incorporated herein by reference for all purposes.

BACKGROUND

Benefits of a closed loop control system for treating diabetic conditions with monitoring glucose levels and adjusting delivery rate of insulin are well known. Such systems, referred to as artificial pancreas, model healthy pancreas which, when functioning normally, produces insulin (by the beta cells (β-cells)) to counteract the rise in glucose levels in the blood stream. As is known, Type-1 diabetes mellitus condition exists when the beta cells in the pancreas either die or are unable to produce sufficient amount of insulin naturally in response to the elevated glucose levels.

Common treatment of Type-1 diabetes is the use of insulin pumps that are programmed to continuously deliver insulin to the body through an infusion set. The use of insulin pumps to treat Type-2 diabetes (where the beta cells in the pancreas do produce insulin, but an inadequate quantity) is also becoming more prevalent. Such insulin delivery devices are preprogrammed with delivery rates such as basal profiles which are tailored to each user, and configured to provide the needed insulin to the user. Additionally, the preprogrammed delivery rates may be supplemented with periodic administration of bolus dosages of insulin (for example, correction bolus or carbohydrate bolus) as may be needed by the user.

In addition, continuous glucose monitoring systems have been developed to allow real time monitoring of fluctuation in glucose levels. One example is the FreeStyle Navigator® Continuous Glucose Monitoring System available from Abbott Diabetes Care Inc., of Alameda, Calif. The use of such glucose monitoring systems provides the user with real time glucose level information. Using the continuous glucose monitoring system, for example, diabetics are able to determine when insulin is needed to lower glucose levels or when additional glucose is needed to raise the level of glucose.

With the continued rise in the number of diagnosed diabetic conditions, there is on-going research to develop closed loop control systems to automate the insulin delivery based on the real time monitoring of the fluctuation in the glucose levels. Closed loop control algorithms such as, for example, proportional, plus integral, plus derivative (PID) control algorithm or model predictive control algorithm exist and are used to control the automatic delivery of insulin based on the glucose levels monitored. One key concern in such automated systems is safety. For example, the glucose sensor in the closed loop control system may enter failure mode (permanently or temporarily) in which case the monitored glucose level in the closed loop control system will introduce error and potentially result in undesirable or dangerous amount of insulin being administered. Additionally, the infusion component in the closed loop control system may have errors or experience failure modes that results in an inaccurate amount of insulin delivered to the user.

Indeed, safety considerations as well as accuracy considerations to address and/or minimize the potential unreliability in the components of the closed loop control system are important to provide a robust control system in the treatment of diabetic conditions.

SUMMARY

In one aspect, there is provided a method and device for monitoring a plurality of parameters associated with a closed loop control operation including continuously monitoring a physiological condition and automatic administration of a medication, detecting an adverse condition associated with the monitored physiological condition or the medication administration deviating from a predetermined safety level of the closed loop control operation, and initiating a non-zero pre-programmed medication delivery rate.

Also provided are systems and kits.

DETAILED DESCRIPTION

Figure 1:
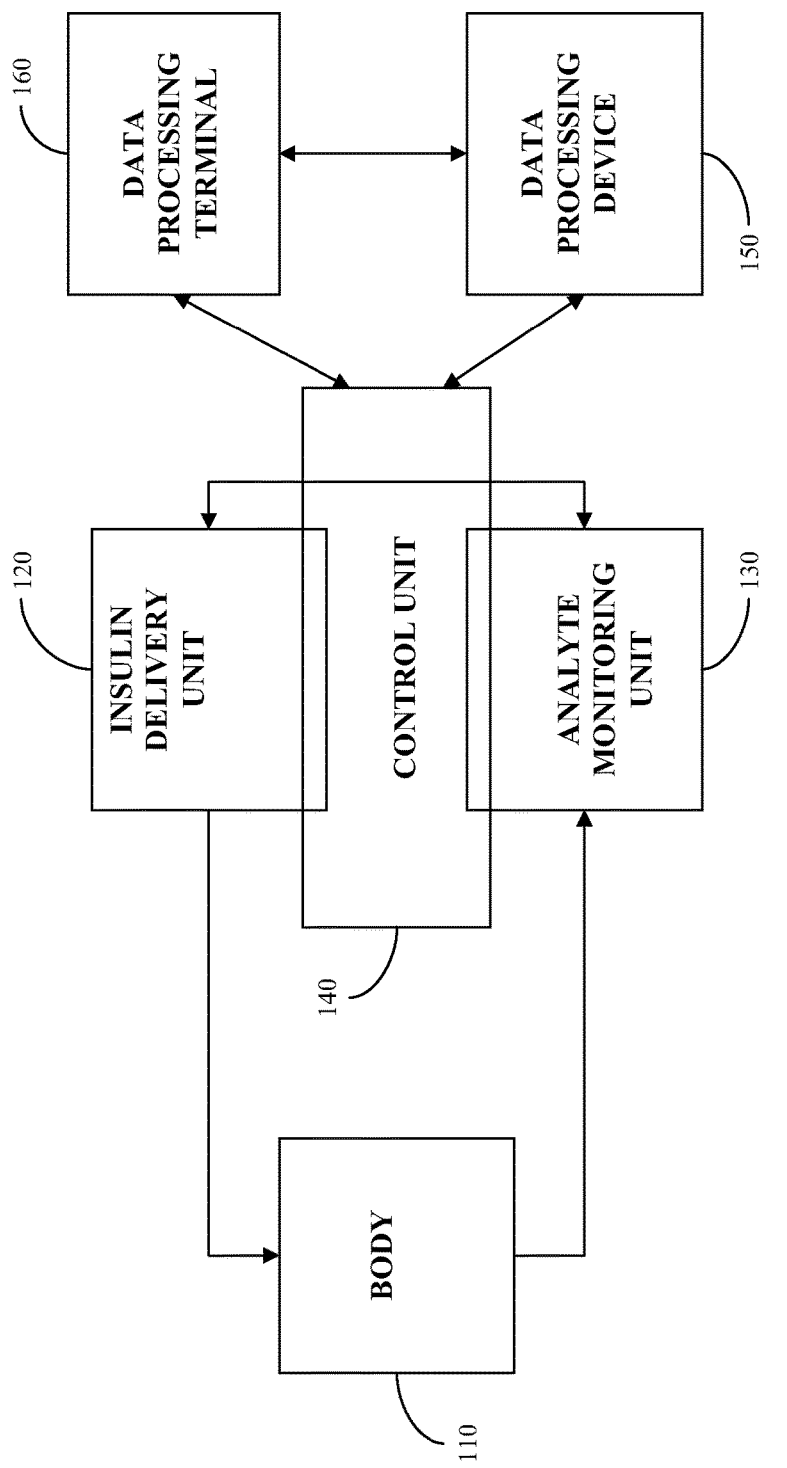
FIG. 1 is a block diagram illustrating an overall closed loop control system in accordance with one embodiment of the present disclosure.

Before embodiments of the present disclosure are described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Generally, embodiments of the present disclosure relate to methods and system for a robust closed loop control system with safety parameters for continuously monitoring at least one analyte such as glucose in body fluid and delivering a suitable level of medication such as insulin. In certain embodiments, the present disclosure relates to the continuous and/or automatic in vivo monitoring of the level of an analyte using an analyte sensor, and under the control of a closed loop control algorithm, determining and delivering an appropriate level of medication such as insulin in response to the monitored analyte level.

Embodiments include medication delivery devices such as external infusion pumps, implantable infusion pumps, on-body patch pump, or any other processor controlled medication delivery devices that are in communication with one or more control units which also control the operation of the analyte monitoring devices. The medication delivery devices may include one or more reservoirs or containers to hold the medication for delivery in fluid connection with an infusion set, for example, including an infusion tubing and/or cannula. The cannula may be positioned so that the medication is delivered to the user or patient at a desired location, such as, for example, in the subcutaneous tissue under the skin layer of the user.

Embodiments include analyte monitoring devices and systems that include an analyte sensor—at least a portion of which is positionable beneath the skin of the user—for the in vivo detection, of an analyte, such as glucose, lactate, and the like, in a body fluid. Embodiments include wholly implantable analyte sensors and analyte sensors in which only a portion of the sensor is positioned under the skin and a portion of the sensor resides above the skin, e.g., for contact to a transmitter, receiver, transceiver, processor, etc.

A sensor (and/or a sensor insertion apparatus) may be, for example, configured to be positionable in a patient for the continuous or periodic monitoring of a level of an analyte in a patient's dermal fluid. For the purposes of this description, continuous monitoring and periodic monitoring will be used interchangeably, unless noted otherwise.

The analyte level may be correlated and/or converted to analyte levels in blood or other fluids. In certain embodiments, an analyte sensor may be configured to be positioned in contact with dermal fluid to detect the level of glucose, which detected glucose may be used to infer the glucose level in the patient's bloodstream. For example, analyte sensors may be insertable through the skin layer and into the dermal layer under the skin surface at a depth of approximately 3 mm under the skin surface and containing dermal fluid. Embodiments of the analyte sensors of the subject disclosure may be configured for monitoring the level of the analyte over a time period which may range from minutes, hours, days, weeks, months, or longer.

Of interest are analyte sensors, such as glucose sensors, that are capable of in vivo detection of an analyte for about one hour or more, e.g., about a few hours or more, e.g., about a few days of more, e.g., about three or more days, e.g., about five days or more, e.g., about seven days or more, e.g., about several weeks or at least one month. Future analyte levels may be predicted based on information obtained, e.g., the current analyte level at time, the rate of change of the analyte, etc. Predictive alarms may notify the control unit (and/or the user) of predicted analyte levels that may be of concern in advance of the analyte level reaching the future level. This enables the control unit to determine a priori a suitable corrective action and implement such corrective action.

FIG. 1 is a block diagram illustrating an overall closed loop control system in accordance with one embodiment of the present disclosure. Referring to FIG. 1, in one aspect, the closed loop control system 100 includes an insulin delivery unit 120 that is connected to a body 110 of a user or patient to establish a fluid path to deliver medication such as insulin. In one aspect, the insulin delivery unit 120 may include an infusion tubing fluidly connecting the reservoir of the delivery unit 120 to the body 110 using a cannula with a portion thereof positioned in the subcutaneous tissue of the body 110.

Referring to FIG. 1, the system 100 also includes an analyte monitoring device 130 that is configured to monitor the analyte level in the body 110. As shown in FIG. 1, a control unit 140 is provided to control the operation of the insulin delivery unit 120 and the analyte monitoring unit 130. In one embodiment, the control unit 140 may be a processor based control unit having provided therein one or more closed loop control algorithm to control the operation of the analyte monitoring device 130 and the delivery unit 120. In one aspect, the control unit 140, the analyte monitoring unit 130 and the delivery unit 120 may be integrated in a single housing. In other embodiments, the control unit 140 may be provided in the housing of the delivery unit 120 and configured for communication (wireless or wired) with the analyte monitoring unit 130. In an alternate embodiment, the control unit may be integrated in the housing of the analyte monitoring unit 130 and configured for communication (wireless or wired) with the delivery unit 120. In yet another embodiment, the control unit 140 may be a separate component of the overall system 100 and configured for communication (wireless or wired) with both the delivery unit 120 and the analyte monitoring unit 130.

Referring back to FIG. 1, the analyte monitoring unit 130 may include an analyte sensor that is transcutaneously positioned through a skin layer of the body 110, and in signal communication with a compact data transmitter provided on the skin layer of the body 110 which is configured to transmit the monitored analyte level substantially in real time to the analyte monitoring unit 130 for processing and/or display. In another aspect, the analyte sensor may be wholly implantable in the body 110 with a data transmitter and configured to wirelessly transmit the monitored analyte level to the analyte monitoring unit 130.

Referring still to FIG. 1, also shown in the overall system 100 is a data processing device 150 in signal communication with the one or more of the control unit 140, delivery unit 120 and the analyte monitoring unit 130. In one aspect, the data processing device 150 may include an optional or supplemental device in the closed loop control system to provide user input/output functions, data storage and processing. Examples of the data processing device 150 include, but not limited to mobile telephones, personal digital assistants (PDAs), in vitro blood glucose meters, Blackberry® devices, iPhones, Palm® devices, data paging devices, and the like each of which include an output unit such as one or more of a display, audible and/or vibratory output, and/or an input unit such as a keypad, keyboard, input buttons and the like, and which are configured for communication (wired or wireless) to receive and/or transmit data, and further, which include memory devices such as random access memory, read only memory, volatile and/or non-volatile memory that store data.

Also shown in the overall system 100 is a data processing terminal 160 which may include a personal computer, a server terminal, a laptop computer, a handheld computing device, or other similar computing devices that are configured to data communication (over the internet, local area network (LAN), cellular network and the like) with the one or more of the control unit 140, the delivery unit 120, the analyte monitoring unit 130, or the data processing device 150, to process, analyze, store, archive, and update information.

It is to be understood that the analyte monitoring device 130 of FIG. 1 may be configured to monitor a variety of analytes at the same time or at different times. Analytes that may be monitored include, but are not limited to, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In the embodiments that monitor more than one analyte, the analytes may be monitored at the same or different times.

Additional detailed descriptions of embodiments of the continuous analyte monitoring device and system, calibrations protocols, embodiments of its various components are provided in U.S. Pat. Nos. 6,175,752; 6,284,478; 7,299,082; U.S. patent application Ser. No. 10/745,878 filed Dec. 26, 2003 entitled "Continuous Glucose Monitoring System and Methods of Use", each incorporated by reference in its entirety for all purposes. Additional detailed description of systems including medication delivery units and analyte monitoring devices, embodiments of the various components are provided in U.S. application patent application Ser. No. 11/386,915, entitled "Method and System for Providing Integrated Medication Infusion and Analyte Monitoring System" disclosure of which are incorporated by reference for all purposes. Moreover, additional detailed description of medication delivery devices and its components are provided in U.S. Pat. No. 6,916,159, the disclosure of which is incorporated by reference for all purposes.

Referring back to FIG. 1, each of the components shown in the system 100 may be configured to be uniquely identified by one or more of the other components in the system so that communication conflict may be readily resolved between the various components, for example, by exchanging or pre-storing and/or verifying unique device identifiers as part of communication between the devices, by using periodic keep alive signals, or configuration of one or more devices or units in the overall system as a master-slave arrangement with periodic bi-directional communication to confirm integrity of signal communication therebetween.

Further, data communication may be encrypted or encoded (and subsequently decoded by the device or unit receiving the data), or transmitted using public-private keys, to ensure integrity of data exchange. Also, error detection and/or correction using, for example, cyclic redundancy check (CRC) or techniques may be used to detect and/or correct for errors in signals received and/or transmitted between the devices or units in the system 100. In certain aspects, data communication may be responsive to a command or data request received from another device in the system 100, while some aspects of the overall system 100 may be configured to periodically transmit data without prompting (such as the data transmitter, for example, in the analyte monitoring unit 130 periodically transmitting analyte related signals).

In certain embodiments, the communication between the devices or units in the system 100 may include one or more of an RF communication protocol, an infrared communication protocol, a Bluetooth enabled communication protocol, an 802.11x wireless communication protocol, internet connection over a data network or an equivalent wireless communication protocol which would allow secure, wireless communication of several units (for example, per HIPAA requirements) while avoiding potential data collision and interference.

In certain embodiments, data processing device 150, analyte monitoring unit 130 and/or delivery unit 120 may include blood glucose meter functions or capability to receive blood glucose measurements. For example, the housing of these devices may include a strip port to receive a blood glucose test strip with blood sample to determine the blood glucose level. Alternatively, a user input device such as an input button or keypad may be provided to manually enter such information. Still further, upon completion of a blood glucose measurement, the result may be wirelessly and/or automatically transmitted to another device in the system 100. For example, it is desirable to maintain a certain level of water tight seal on the housing of the delivery unit 120 during continuous use by the patient or user. In such case, incorporating a strip port to receive a blood glucose test strip may be undesirable. As such, the blood glucose meter function including the strip port may be integrated in the housing of another one of the devices or units in the system (such as in the analyte monitoring unit 103 and/or data processing device 150). In this case, the result from the blood glucose test, upon completion may be wirelessly transmitted to the delivery unit 120 for storage and further processing.

Any suitable test strip may be employed, e.g., test strips that only require a very small amount (e.g., one microliter or less, e.g., 0.5 microliter or less, e.g., 0.1 microliter or less), of applied sample to the strip in order to obtain accurate glucose information, e.g. FreeStyle® or Precision® blood glucose test strips from Abbott Diabetes Care Inc. Glucose information obtained by the in vitro glucose testing device may be used for a variety of purposes, computations, etc. For example, the information may be used to calibrate the analyte sensor, confirm results of the sensor to increase the confidence in the accuracy level thereof (e.g., in instances in which information obtained by sensor is employed in therapy related decisions), determine suitable amount of bolus dosage for administration by the delivery unit 120.

In certain embodiments, a sensor may be calibrated using only one sample of body fluid per calibration event. For example, a user need only lance a body part one time to obtain sample for a calibration event (e.g., for a test strip), or may lance more than one time within a short period of time if an insufficient volume of sample is obtained firstly. Embodiments include obtaining and using multiple samples of body fluid for a given calibration event, where glucose values of each sample are substantially similar. Data obtained from a given calibration event may be used independently to calibrate or combined with data obtained from previous calibration events, e.g., averaged including weighted averaged, etc., to calibrate.

One or more devices or components of the system 100 may include an alarm system that, e.g., based on information from control unit 140, warns the patient of a potentially detrimental condition of the analyte. For example, if glucose is the analyte, an alarm system may warn a user of conditions such as hypoglycemia and/or hyperglycemia and/or impending hypoglycemia, and/or impending hyperglycemia. An alarm system may be triggered when analyte levels reach or exceed a threshold value. An alarm system may also, or alternatively, be activated when the rate of change or acceleration of the rate of change in analyte level increase or decrease reaches or exceeds a threshold rate of change or acceleration. For example, in the case of the glucose monitoring unit 130, an alarm system may be activated if the rate of change in glucose concentration exceeds a threshold value which might indicate that a hyperglycemic or hypoglycemic condition is likely to occur. In the case of the delivery unit 120, alarms may be associated with occlusion conditions, low reservoir conditions, malfunction or anomaly in the fluid delivery and the like. System alarms may also notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

Referring yet again to FIG. 1, the control unit 140 of the closed loop control system 100 may include one or more processors such as microprocessors and/or application specific integrated circuits (ASIC), volatile and/or non-volatile memory devices, and additional components that are configured to store and execute one or more closed loop control algorithms to dynamically control the operation of the delivery unit 120 and the analyte monitoring unit 130. The one or more closed loop control algorithms may be stored as a set of instructions in the one or more memory devices and executed by the one or more processors to vary the insulin delivery level based on, for example, glucose level information received from the analyte sensor.

As discussed in further detail below, the one or more control algorithms of the control unit 140 are configured to monitor parameters and conditions associated with a safety indication of the closed loop control system 100 and generate and notify the user, as may be desirable to perform one or more troubleshooting actions and/or automatically revert to a semi-closed loop control mode or a manual control mode that require some level of user, patient or healthcare provider intervention.

Figure 2:
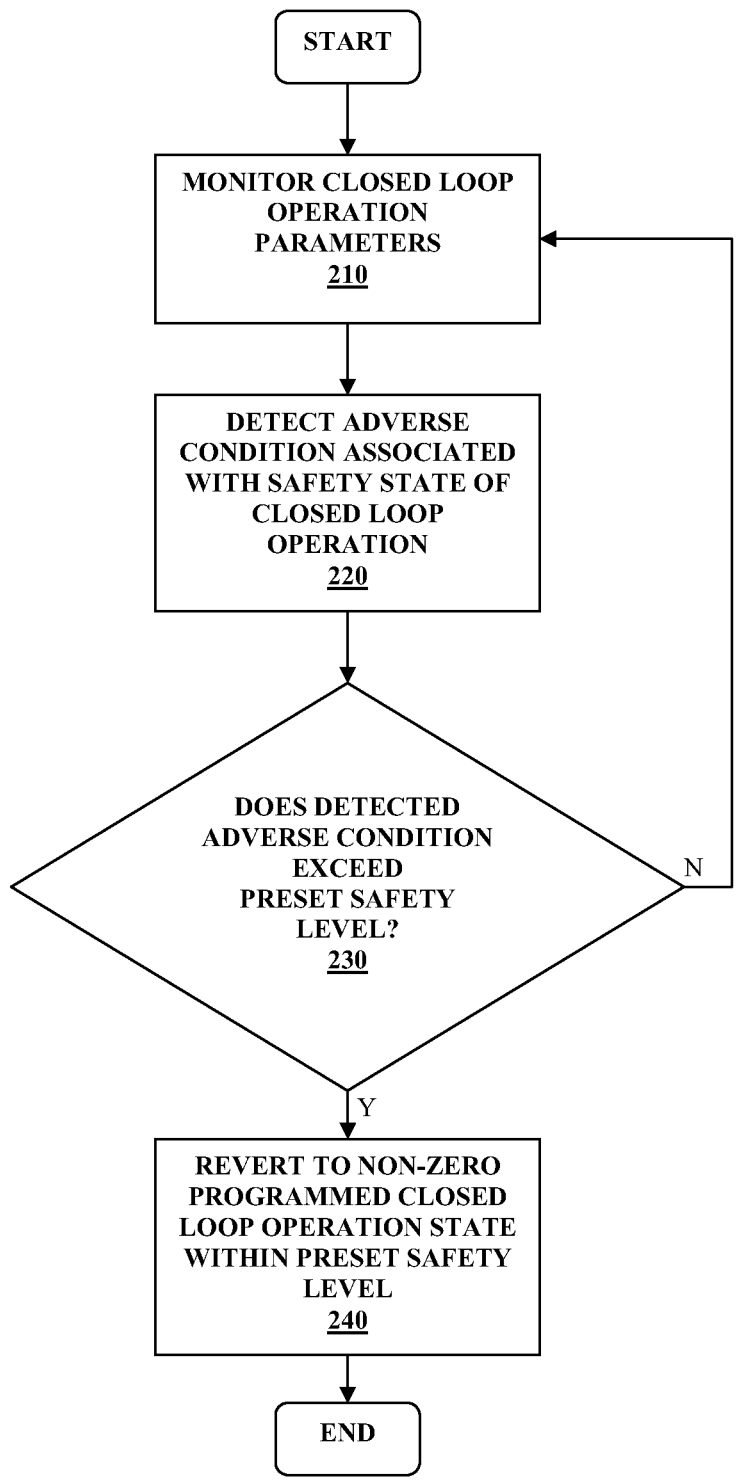
FIG. 2 is a flowchart illustrating adverse condition monitoring and control in a closed loop control system in accordance with one embodiment of the present disclosure.

FIG. 2 is a flowchart illustrating adverse condition monitoring and control in a closed loop control system in accordance with one embodiment of the present disclosure. Referring to FIGS. 1 and 2, in one embodiment, control unit 140 executing the closed loop system control is configured to monitor the closed loop control operation parameters (210). In one aspect, the closed loop control operation parameters may be associated with the operation of the delivery unit 120, and operational conditions associated therewith such as fluid delivery, amount of insulin delivered, potential occlusion and the like. In addition the closed loop control operation parameters monitored may also include operational conditions associated with the analyte monitoring unit 130 such as, for example, the validity or integrity of analyte sensor signals, unanticipated sensor signal drop out, missing sensor data, and the like. Further, in embodiments where the delivery unit 120 and analyte monitoring unit 130 are separate components in the system 100 communicating via wireless connection, monitored control operation parameters may include the integrity of the communication connection between the devices or units in the system 100.

Referring to FIG. 2, when based on the monitored closed loop operation parameters an adverse condition associated with a safety state of the closed loop operation is detected (220), it is determined whether the detected adverse condition exceeds a preset safety level (230). For example, in the case where the adverse condition is associated with the integrity of analyte sensor signals, it is determined whether sufficiently accurate glucose level can be derived based on the received sensor signals (for example, based on extrapolation using previously received sensor data, and/or in conjunction with a rate of change of glucose level determination). The adverse condition detected may also include a determined medication delivery level that exceeds a preset threshold level (for example, a physician determined maximum basal delivery rate for the user). As a further example, the adverse condition detected may include communication failure between the components of the overall system 100 including, the analyte monitoring unit 130 and the delivery unit 120.

Referring back to FIG. 2, when it is determined that the detected adverse condition does not exceed a preset safety level, in one aspect, the control unit 140 is configured to proceed with the execution of the closed loop control algorithm to, based on the real time glucose data received from the analyte monitoring unit 130, adjust the insulin delivery rate from the delivery unit 120, and the routine returns to monitoring the closed loop operation parameters. On the other hand, if it is determined that the detected adverse condition exceeds the preset safety level, the control unit 140 in one embodiment is configured to command or instruct the delivery unit 120 to revert to a non-zero pre-programmed closed loop operation state within the safety level (240). For example, when it is determined that the determined insulin level for delivery exceeds the safety level or maximum delivery rate (for example, established by a physician or healthcare provider, or the user, and programmed and stored in the control unit 140), the control unit 140 is configured to automatically revert to an insulin delivery rate that is within the safety level so that potential over-dosing may be avoided.

In another aspect, the control unit 140 may be configured to issue a command to the delivery unit 120 every 15 minutes (or some other predetermined time interval) which sets insulin delivery rate for a 20 minute time period (or some other suitable time period). In the event that the adverse condition exceeding the preset safety level is detected preventing the control unit 140 from issuing a new command to the delivery unit 120 during the 20 minute time period, the control unit 140 is configured to instruct the delivery unit 120 to revert to a pre-programmed delivery rate that is within the safety level (for example, a less amount of insulin to be delivered). In a further aspect, the detected adverse condition may include a determination of insulin on board value that, in conjunction with the insulin amount to be delivered exceeds the upper safety level of insulin delivery, the control unit 140 may be configured to revert to or switch to a preset or pre-programmed level that would bring the insulin delivery amount to be within the determined safety level.

As discussed, in one aspect, the insulin delivery amount that is within the safety level may be pre-programmed in the control unit 140, for example, and implemented as part of the closed loop control to automatically deliver the insulin amount based on the pre-programmed level. In a further aspect, the control unit 140 may be configured to modify or adjust the existing insulin delivery rate that is within the safety level in response to the detected adverse condition, (for example, reducing the determined insulin delivery rate by a certain factor such as 75%, to maintain the insulin delivery amount within the safety level).

In this manner, in one aspect, when an adverse condition associated with the safety state of the closed loop control operation is detected, the control unit 140 may be configured to operate within a predefined safety range rather than requesting user intervention or disabling the closed loop control operation to revert to a manual control operation mode. While certain examples of adverse conditions are discussed above, within the scope of the present disclosure, any other condition associated with the safety level in the operation of the closed loop control system 100 are contemplated, the detection of any of which initiates the evaluation of the detected condition and appropriate modification to the closed loop control system parameters to continue operation of the closed loop control operation without prematurely disabling the system, while maintaining the desired level of safety in using the closed loop control system 100.

Figure 3:
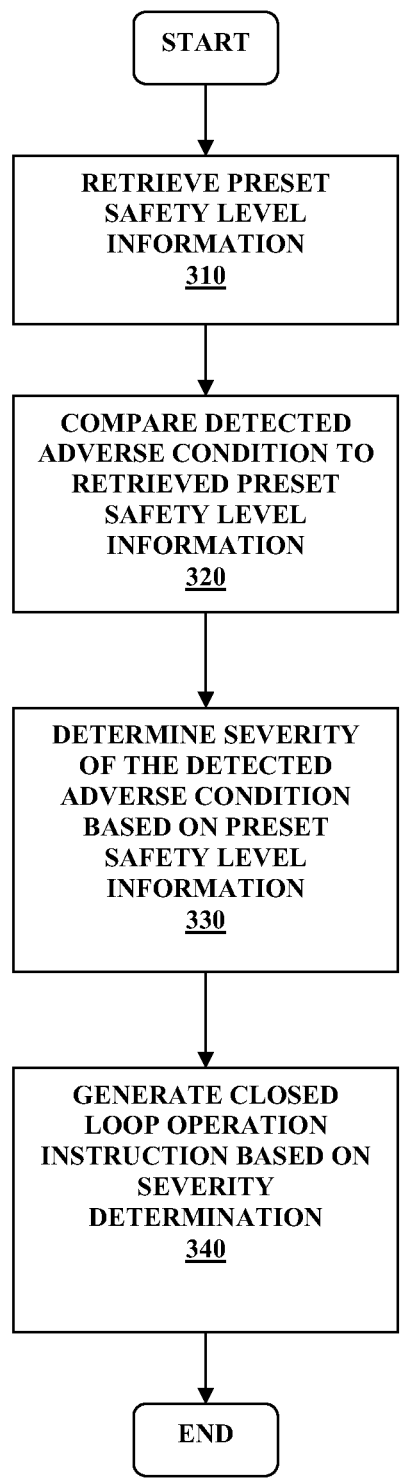
FIG. 3 is a flowchart illustrating adverse condition monitoring and control in a closed loop control system in accordance with another embodiment of the present disclosure.

FIG. 3 is a flowchart illustrating adverse condition monitoring and control in a closed loop control system in accordance with another embodiment of the present disclosure. Referring to FIGS. 1 and 3, in one embodiment, control unit 140 (FIG. 1) retrieves a preset safety level information (310) and compares the retrieved preset safety level information to one or more detected adverse condition (320). Thereafter, a level of severity associated with the detected adverse condition is determined based, at least in part on the retrieved preset safety level information (330). After determining the severity level, the control unit 140 is configured to generate one or more closed loop operation instructions based on the determined severity level for execution (340).

That is, in one aspect, when an adverse condition is detected by the control unit 140, the control unit 140 (FIG. 1) is configured in one aspect to determine how severe is the detected adverse condition with respect to the automated insulin delivery. For example, control unit 140 may detect a communication failure from the transmitter of the analyte monitoring unit 130 and thus not receive a current sensor data indicative of the glucose level. However, the control unit 140 may have stored in one or more of its memory units previously received glucose levels from the transmitter of the analyte monitoring unit 130. Given an insulin delivery rate that is within the safety level, and a relatively stable glucose value (for example, based on a rate of change of glucose determination from previously received glucose data), the control unit 140 may be configured to declare the communication failure as a non-critical adverse condition detected. In this manner, the generated closed loop operation instruction (340) may not modify the current delivery rate by the delivery unit 120 (FIG. 1).

On the other hand, if the rate of change of the glucose level indicated by previously received sensor data demonstrates a rapid variation in the glucose level, and/or the communication failure persists over a time period that exceeds a certain level (for example, exceeding 20 minutes or some other suitable time frame), the generated closed loop operation instruction (340) may include commands to the delivery unit 120 (FIG. 1) to modify the delivery rate and/or revert to a pre-programmed delivery rate that are within the previously determined safety level. In one aspect, the control unit 140 (FIG. 1) may be configured to continuously monitor the presence of the detected adverse condition until the condition is corrected, in which case, the generated closed loop operation instruction (340) may include commands to the delivery unit 120 to return to the prior closed loop control operation.

Figure 4:
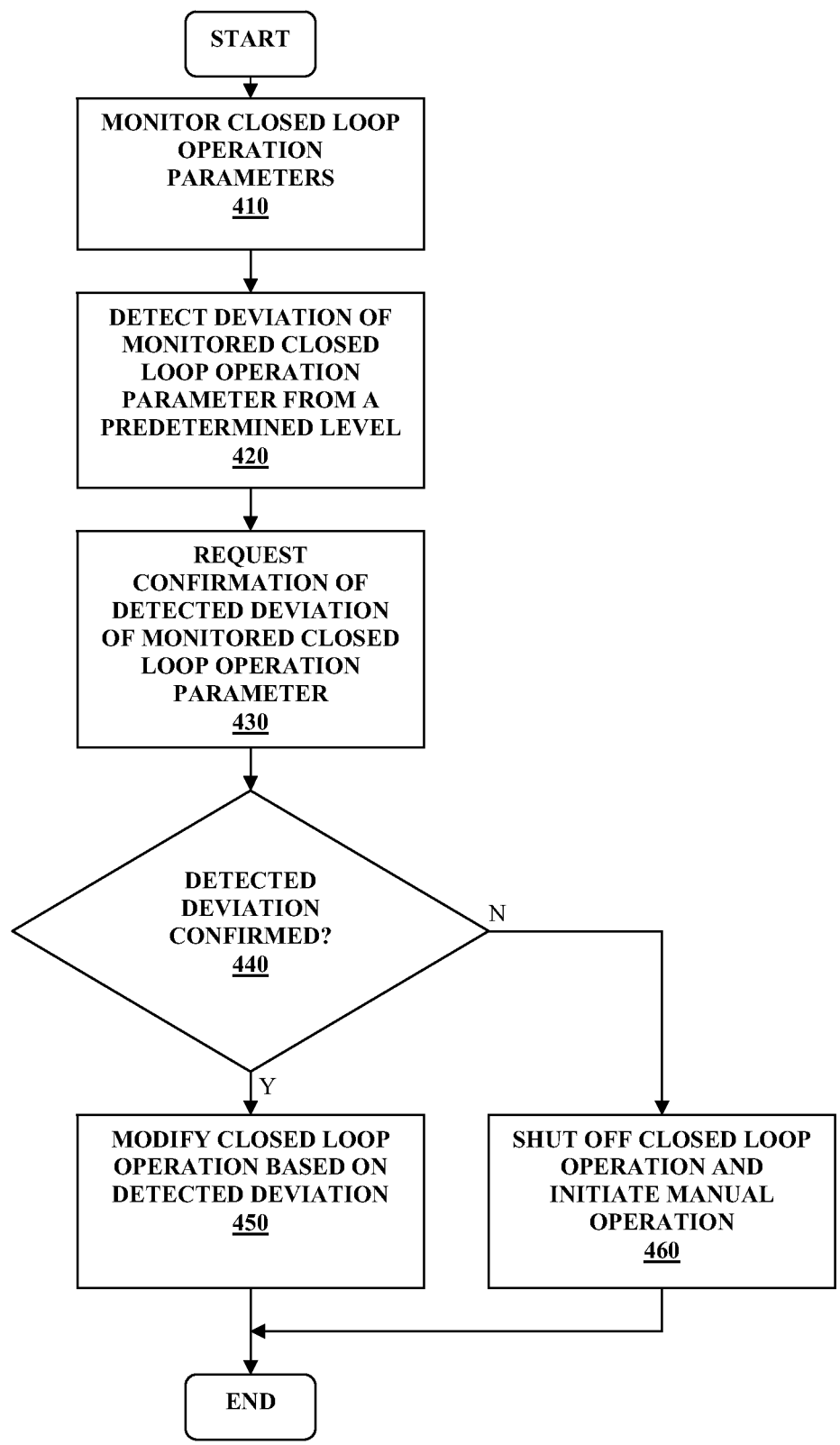
FIG. 4 is a flowchart illustrating condition deviation monitoring and control in a closed loop control system in accordance with one embodiment of the present disclosure.

FIG. 4 is a flowchart illustrating condition deviation monitoring and control in a closed loop control system in accordance with one embodiment of the present disclosure. Referring to FIGS. 1 and 4, in another aspect, control unit 140 (FIG. 1) monitors the closed loop operation parameters (410) and when it detects one or more monitored closed loop operation parameters deviating from a predetermined level (420), the control unit 140 (FIG. 1) may be configured to generate and output a request for confirmation of the detected deviation of the monitored closed loop operation parameter (430).

For example, in the closed loop control system 100 (FIG. 1), a user interface such as a display unit or audible/vibratory notification in the insulin delivery unit 120 and/or the analyte monitoring unit 130 may indicate a notification for the user to confirm the presence of the detected deviation of the monitored closed loop operation parameter. Referring to FIG. 4, if the detected deviation of the monitored closed loop operation parameter is confirmed (440), in one aspect, the control unit 140 (FIG. 1) may be configured to modify the closed loop control operation based on the detected deviation of one or more of its parameters (450). On the other hand, if the presence of the detected deviation of the monitored closed loop operation parameter is not confirmed, then the control unit 140 (FIG. 1) may be configured to disable the closed loop control operation, and initiate a manual operation mode (460) to deliver insulin by the delivery unit 120 (FIG. 1).

In this manner, in one aspect, the control unit 140 (FIG. 1) may be configured to request for user confirmation or verification of the presence of the detected adverse condition prior to initiating responsive corrective action, and further, when no verification or confirmation is received, for example, within a set time period, the control unit 140 (FIG. 1) may be configured to disable the closed loop control operation. Accordingly, certain adverse conditions detected may prompt the control unit 140 (FIG. 1) to request confirmation prior to automatically responding to such occurrence of adverse condition, and further, when no confirmation is received, the control unit 140 (FIG. 1) may temporarily revert to a semi-closed loop or non-closed loop manual delivery mode. In this manner, in certain aspects, a level of safety in using the closed loop control system 100 is maintained, and depending upon the particular detected adverse condition, the control unit 140 may automatically, temporarily adjust the delivery mode of the delivery unit 120 (FIG. 1), or alternatively, require user intervention.

Furthermore, within the scope of the present disclosure, while the detected conditions are described as adverse conditions, any parameter or condition associated with the operation of the closed loop control system 100 are contemplated including but not limited to, analyte sensor operation, sensor signal filtering, sensor signal level, sensor calibration, sensor signal attenuation, communication failure, signal outlier condition, rate of change of the glucose level, insulin delivery rate, insulin on board information, type of insulin, duration of the closed loop control operation, number or frequency of bolus dosage administration, predicted or projected glucose level and/or the direction of the predicted or projected glucose level, frequency of blood glucose measurements, maximum or minimum insulin delivery level, for example.

Figure 5:
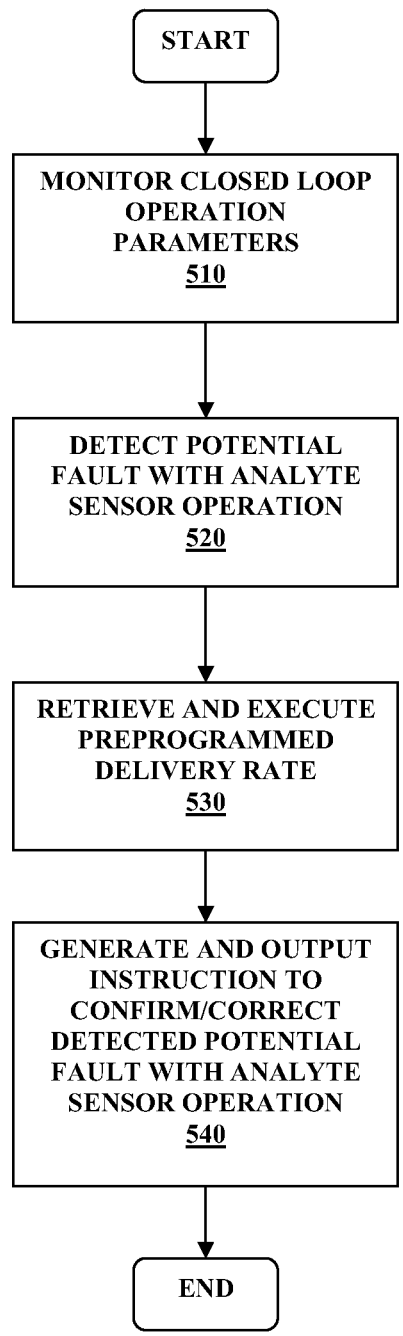
FIG. 5 is a flowchart illustrating analyte sensor condition monitoring and control in a closed loop control system in accordance with one embodiment of the present disclosure.

FIG. 5 is a flowchart illustrating analyte sensor condition monitoring and control in a closed loop control system in accordance with one embodiment of the present disclosure. Referring to FIGS. 1 and 5, in one embodiment, control unit 140 (FIG. 1) is configured to monitor closed loop operation parameters (510) in the closed loop control system 100 (FIG. 1). When a potential fault or failure mode associated with the operation of the analyte sensor is detected (520), the control unit 140 is configured to retrieve and execute a preprogrammed delivery rate (530) (for example, a predetermined basal profile), while maintaining the closed loop control operation mode. Further, the control unit 140 is configured to generate and output instructions or request to confirm and/or correct the detected potential fault or failure mode of the analyte sensor (540).

That is, in one aspect, the closed loop control operation is not disabled when it is initially detected that the analyte sensor may not be properly functioning. Rather, the closed loop control operation includes the execution of a preprogrammed delivery rate that is determined to be within a safety level, and when the potential fault condition or failure mode has been corrected, the control unit 140 may be configured to terminate the execution of the pre-programmed delivery rate and resume real time automatic adjustment to the insulin delivery rate based on the analyte sensor signals.

In this manner, rather than prematurely terminating the operation of the closed loop control system 100 at a first indication of potential failure or fault of the analyte sensor, in one aspect, the control unit 140 is configured to instruct the delivery unit 120 to execute a predetermined delivery rate that is within the safety level until corrective action related to the analyte sensor (for example, replacing the sensor, or recalibrating the sensor with a blood glucose measurement) is performed. In a further aspect, the control unit 140 may be configured to modify the retrieved predetermined delivery rate based on the insulin delivered (for example, to consider the insulin on board level) so that the safety level associated with the amount of insulin to be delivered is maintained.

Figure 6:
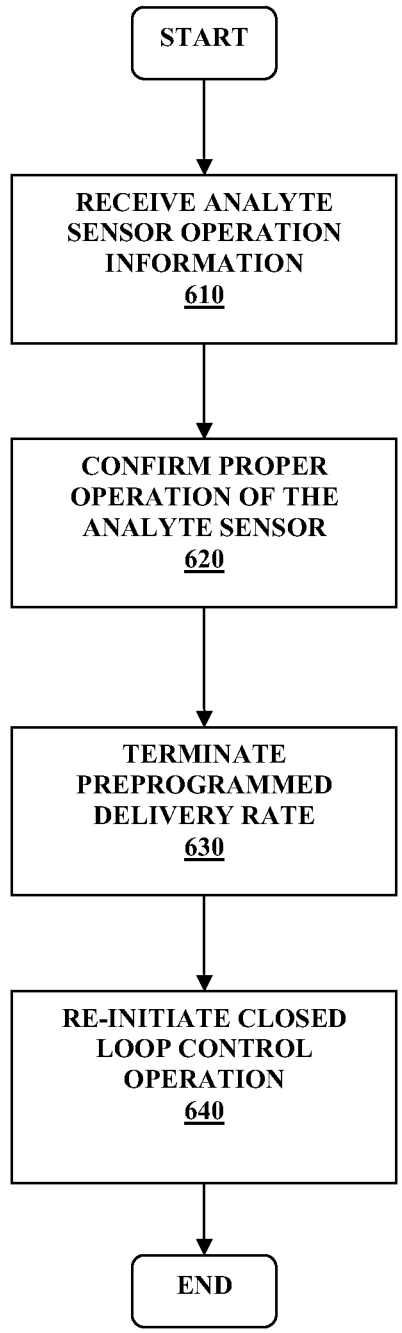
FIG. 6 is a flowchart illustrating analyte sensor condition monitoring and control in a closed loop control system in accordance with another embodiment of the present disclosure.

FIG. 6 is a flowchart illustrating analyte sensor condition monitoring and control in a closed loop control system in accordance with another embodiment of the present disclosure. Referring to FIGS. 1 and 6, in another aspect, when the control unit 140 receives analyte sensor operation information (610), one or more routines are performed to confirm the proper operation of the analyte sensor (620). For example, the control unit 140 may be configured to verify the calibration information of the analyte sensor so that the value level derived therefrom accurately indicates the monitored glucose level.

In a further aspect, the control unit 140 may be configured to retrieve the most recent sensor sensitivity determination based, for example, on the reference blood glucose measurement received, and to compare the retrieved sensitivity to a stored nominal sensitivity for the sensor to confirm a variation between sensitivities not exceeding a predetermined level. In another aspect, when a scheduled calibration event occurs to calibrate the analyte sensor, the current blood glucose measurement is used to determine an updated sensor sensitivity value which may be used in conjunction with one or more prior sensitivity values or nominal sensitivity value.

Referring back to FIG. 6, when it is confirmed that the analyte sensor is in proper operation mode, the preprogrammed delivery rate executed by the delivery unit 120 (FIG. 1) initiated when the sensor potential failure mode was detected, is terminated (630), and the closed loop control operation based on the analyte sensor signals is re-initiated (640).

In the manner described above, in accordance with embodiments of the present disclosure, the operation of the closed loop control system 100 may include monitoring the condition or parameters associated with the analyte monitoring unit 130 and for example, the analyte sensor, and execute one or more routines to instruct the delivery unit 120 to temporarily execute preprogrammed or modified delivery profile determined to be within the safety limits, or to disable the closed loop control operation to maintain the desired degree of safety in using the closed loop control system 100 (FIG. 1). Indeed, in one aspect, for example, when an analyte sensor reading erroneously indicates a high level of glucose which is a false positive value and where the actual glucose level is lower than the measured high level of glucose, aspects of the closed loop control operation are configured to establish a limit in the amount of insulin delivered so that when sensor failure is detected, delivery of insulin amount beyond the determined safe level is prevented.

Figure 7:
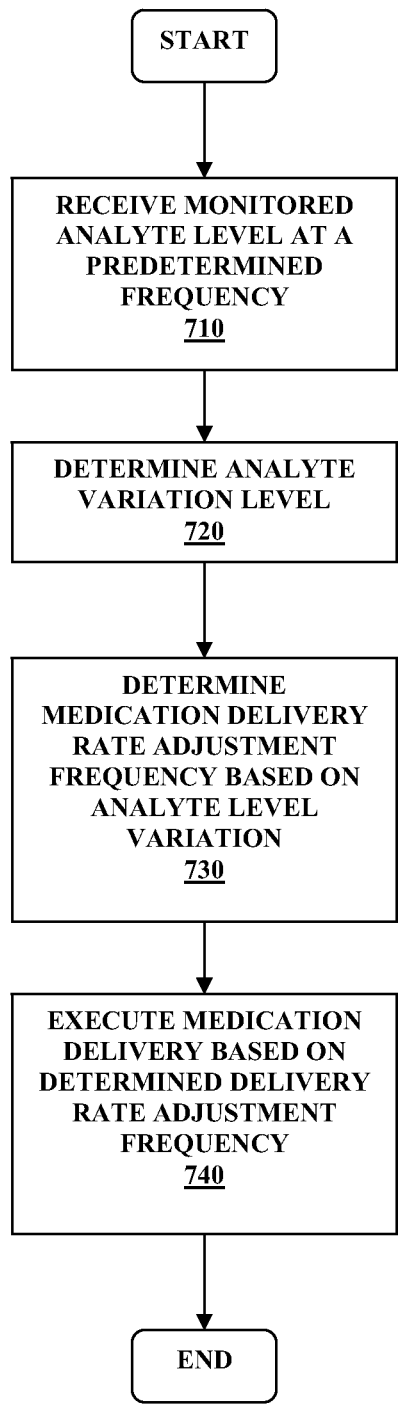
FIG. 7 is a flowchart illustrating variable rate control in a closed loop control system in accordance with one embodiment of the present disclosure.

FIG. 7 is a flowchart illustrating variable rate control in a closed loop control system in accordance with one embodiment of the present disclosure. Referring to FIGS. 1 and 7, in one aspect, control unit 140 executing the closed loop control algorithm in the closed loop control system 100 receives monitored analyte level at a predetermined frequency (710). Based at least in part on the received monitored analyte level, the analyte variation level is determined (720). Thereafter, as shown, the medication delivery rate adjustment frequency is determined based on the determined analyte variation level (730), and thereafter, the delivery unit 120 (FIG. 1) is instructed to deliver the medication at the determined medication delivery rate adjustment frequency (740). That is, in one aspect, the rate of monitored glucose level is associated with the adjustment of the frequency in which to instruct the delivery unit 120 to deliver insulin.

For example, in one aspect, the control unit 140 may be configured to monitor the glucose level from the analyte monitoring unit 130 at a higher frequency (such as, for example once per minute), and also, adjust the rate of insulin delivery by the delivery unit 120 (FIG. 1) at a lower frequency (for example, once every 15 minutes). Indeed, it may be unnecessary to adjust the rate of insulin delivery more frequently than once every 15 minutes when the monitored glucose level (at a higher frequency) does not indicate significant variation in the glucose level. Accordingly, control unit 140 may be configured to issue an instruction or command to the delivery unit 120 once every 15 minutes (or some other suitable interval) to vary the delivery rate based on the glucose level.

One advantage resulting from the less frequent delivery rate adjustment is the conservation of power in the control unit 140 and/or the delivery unit 120. That is, battery power may be conserved by avoiding the generation, communication and/or execution of instructions or commands associated with determining and implementing modification to the insulin delivery rate. On the other hand, since the glucose level is monitored every minute (or at a more frequent time interval), control unit 140 is configured to monitor the variation in the glucose level monitored, and as long as the variation is within a threshold level, the corresponding insulin level delivery adjustment determination is not executed with the same or similar frequency.

However, when the variation in the monitored glucose level exceeds the predetermined threshold level indicating a large variation in the monitored glucose level, or in the cases where a meal event or carbohydrate intake event occurs which will impact the monitored glucose level, it may be desirable to adjust the rate of insulin delivery to be more frequent (for example, adjustment to the delivery rate once every 5 minutes rather than 15 minutes, or with each determination of the glucose level). In this manner, to the extent that adjustment to the insulin delivery rate is desirable, the frequency of the adjustment may be associated with the monitored glucose level such that, for example, control unit 140 may be configured to determine, with each received glucose value, whether adjustment to the insulin delivery rate is needed.

Figure 8:
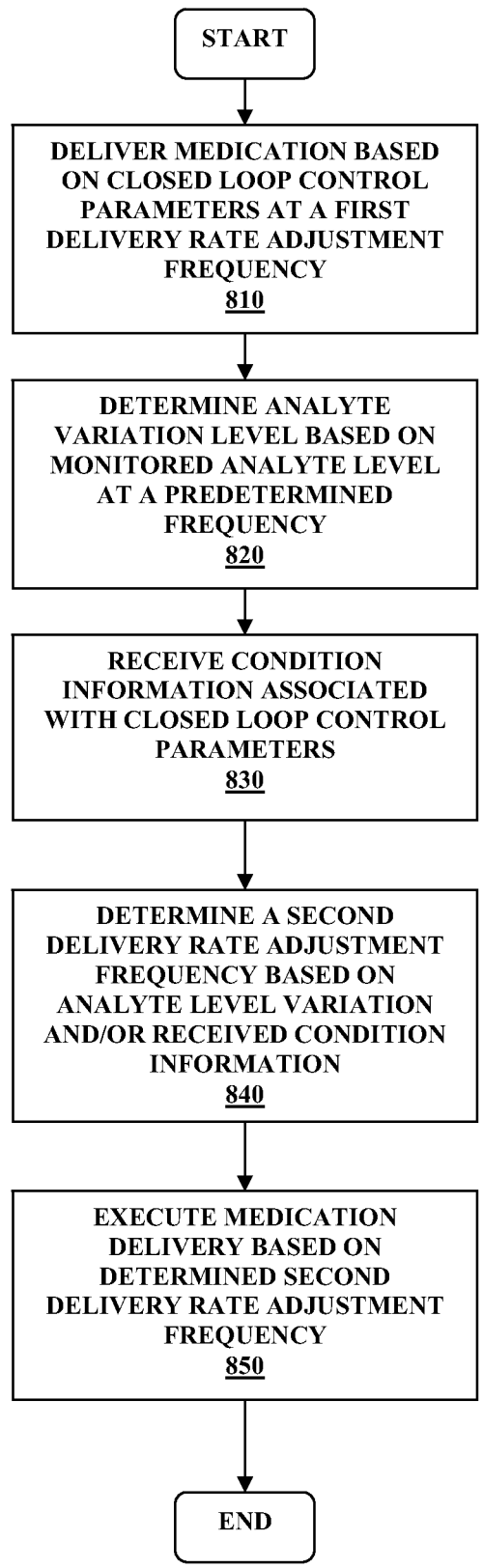
FIG. 8 is a flowchart illustrating variable rate control in a closed loop control system in accordance with another embodiment of the present disclosure.

FIG. 8 is a flowchart illustrating variable rate control in a closed loop control system in accordance with another embodiment of the present disclosure. Referring to FIGS. 1 and 8, control unit 140 (FIG. 1) in one aspect may be configured to instruct the delivery unit 120 (FIG. 1) to deliver medication based on closed loop control parameters at a first delivery rate adjustment frequency (810). Thereafter, the analyte variation level is determined based on the monitored analyte level at a predetermined frequency (820). Referring back to FIG. 8, one or more condition information (for example, but not limited to an anticipated meal event) associated with the closed loop control parameters is received (830). Thereafter, a second delivery rate adjustment frequency is determined based on the analyte level variation and/or received condition information (840), and the medication delivery is executed (for example, by the insulin delivery unit 120 (FIG. 1)) at the determined second delivery rate adjustment frequency (850).

In this manner, in one aspect, control unit 140 is configured to maximize responsiveness to substantial variation in monitored glucose level, or in anticipation of variation in glucose level, while providing lower power requirements for the various components of the system 100 (FIG. 1). Within the scope of the present disclosure, other suitable time intervals or frequency may be used for the glucose monitoring, and further, the associated adjustment to the insulin delivery rate.

That is, embodiments of the present disclosure allow for lower rate of control commands, for example, where the delivery unit 120 and the analyte monitoring unit 130 are configured in the system 100 as separate components, with the control unit 140 provided with the analyte monitoring unit 130 and communicating wirelessly with the delivery unit 120, and each being powered by a respective power supply such as a battery.

Figure 9:
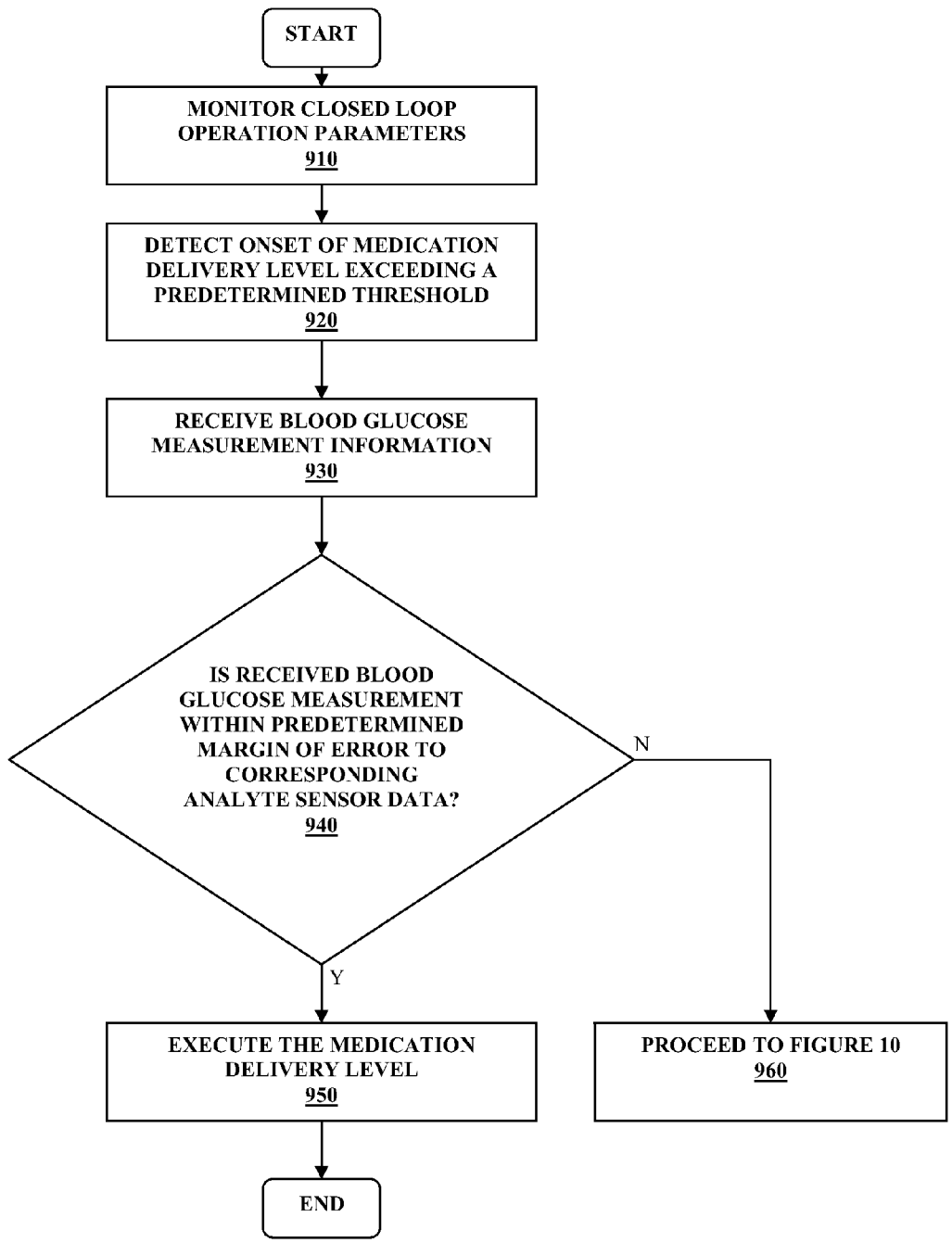
FIGS. 9-10 are flowcharts illustrating blood glucose measurement to improve accuracy of the closed loop control system in accordance with another embodiment of the present disclosure.
Figure 10:
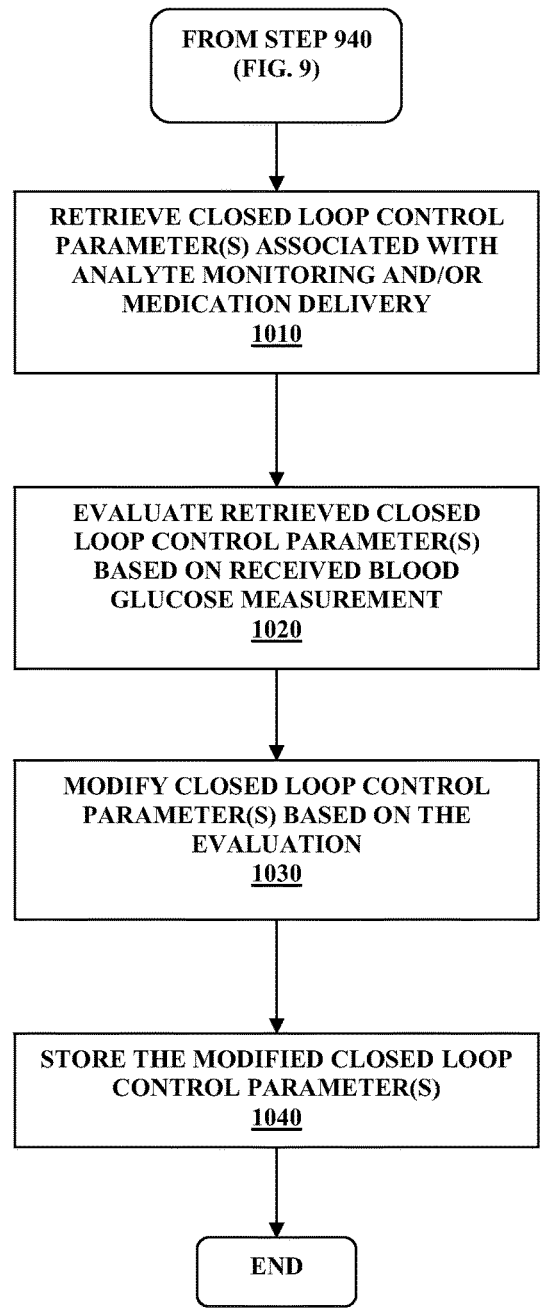

FIGS. 9-10 are flowcharts illustrating blood glucose measurement to improve accuracy of the closed loop control system in accordance with another embodiment of the present disclosure. Referring to FIGS. 1, 9 and 10, closed loop operation parameters are monitored (910) and when onset of medication delivery level (for example, a large insulin dosage level) that exceeds a predetermined threshold level is detected (920), blood glucose measurement information is received (930) (for example, from a blood glucose meter or manually entered by user input). Based on the received blood glucose measurement information, it is determined whether the received blood glucose measurement is within a predetermined margin of error to a time corresponding analyte sensor data (940). In other words, it is determined whether the sensor data correlates to the blood glucose measurement within a predetermined margin of error.

Referring back to FIG. 9, if it is determined that the analyte sensor data and the blood glucose measurement are within the predetermined margin of error, then the detected onset of medication delivery level is maintained and the delivery unit 120 delivers that level of medication (950). On the other hand, if it is determined that the blood glucose measurement received is not within the predetermined margin of error (940), then referring back to FIG. 10 (960), the closed loop control parameters associated with the analyte monitoring and/or the medication delivery are retrieved (1010), and the retrieved closed loop control parameters are evaluated based on the received blood glucose measurement (1020).

For example, one or more of the closed loop control parameters retrieved may include a request for an additional blood glucose measurement value, an instruction to modify or adjust insulin delivery rate, command to disable closed loop control operation and initiate semi-closed loop control operation or manual control operation, or instruction to recalibrate the analyte sensor, among others. Referring back to FIG. 10, upon evaluation of the retrieved one or more closed loop control parameters, the retrieved one or more parameters may be modified (1030) and thereafter the modified one or more closed loop control parameters is stored (1040).

In this manner, for example, under the control of the control unit 140 (FIG. 1) executing the closed loop control algorithm, when it is detected that a large amount of insulin is to be delivered by the delivery unit 120, the control unit 140, as a safety measure, for example, may prompt the user to enter a current blood glucose measurement (for example, using an in vitro blood glucose meter), to confirm and/or verify the accuracy of the analyte sensor level from the analyte monitoring unit 130 based on which the large amount of insulin to be delivered was determined for execution. For example, a Kalman filter may be used as part of the control unit 140 to process the analyte sensor data and the received blood glucose measurement to optimally adjust the insulin level.

In one aspect, the request or prompt to enter the blood glucose measurement may be initiated when the determined insulin amount for delivery in the closed loop control system 100 exceeds a predetermined safety level established, for example, by a healthcare provider or physician, where the safety level includes, for example, the highest insulin delivery rate without blood glucose measurement confirmation. Within the scope of the present disclosure, other conditions or parameters may be used to trigger the request for blood glucose measurement for confirming sensor accuracy, glucose level verification, and the like.

Further, in another aspect, the control unit 140 may be configured to discontinue requesting blood glucose measurements (even when the insulin level to be delivered exceeds the predetermined safety level) when a predetermined number of successful blood glucose measurement confirmations have occurred and the analyte sensor is considered accurate and stable. Still another aspect of the present disclosure includes modifying the safety level for the highest rate of insulin delivery based on the determination of sensor stability and accuracy in view of, for example, successive confirmation of blood glucose measurements to the corresponding sensor values.

Figure 11:
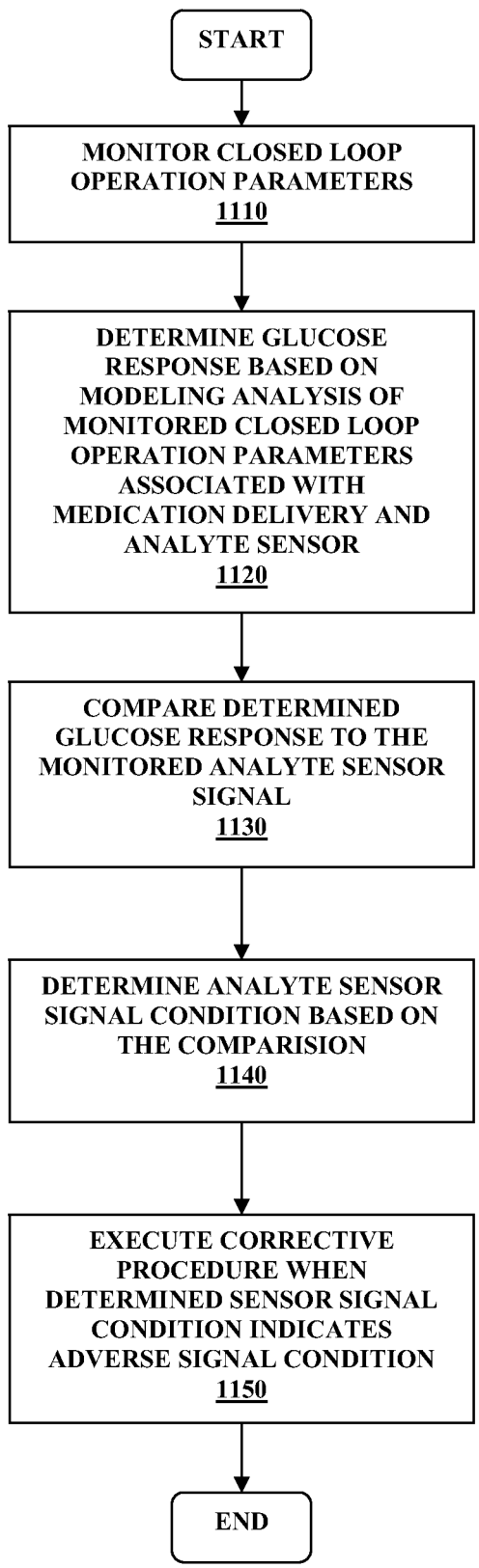
FIG. 11 is a flowchart illustrating medication delivery information to determine analyte sensor condition in a closed loop control system in accordance with one embodiment of the present disclosure.

FIG. 11 is a flowchart illustrating medication delivery information to determine analyte sensor condition in a closed loop control system in accordance with one embodiment of the present disclosure. Referring to FIGS. 1 and 11, in the closed loop control operation state of the closed loop control system 100, control unit 140 (FIG. 1) in one aspect monitors closed loop operation parameters (1110) and performs a predictive modeling analysis of the monitored closed loop control operation parameters associated with the medication delivery and analyte sensor to determine a predictive glucose response (1120). Thereafter, the determined predictive glucose response is compared with the corresponding monitored analyte sensor signal (1130) and a sensor signal condition based on the comparison is determined (1140). For example, based on the comparison, the sensor signal condition may indicate a signal attenuation condition of the glucose sensor. Referring back to FIG. 11, when the sensor signal condition indicates an adverse signal condition or a condition associated with a corrective action or procedure, the corresponding corrective procedure is retrieved and executed by the control unit 140 (1150).

In this manner, in one aspect, using the insulin delivery information, and based on a predictive model implemented to determine a modeled glucose sensor signal, the robustness of the closed loop control system 100 may be enhanced and accuracy of the overall system 100 improved. In one aspect, the predictive model used may include a routine or algorithm that describes glucose response or behavior based on one or more exogenous factors including, among others, insulin delivery information, meal intake, exercise events, and the like, as well as prior monitored sensor data. Accordingly, in one aspect, real time insulin delivery information may be used to improve glucose sensor anomalies such as signal dropouts and early signal attenuation.

For example, as discussed above, the generated modeled glucose sensor response is compared in one aspect to the actual measured sensor data, and based on the comparison, it may be determined that anomalies exist with the glucose sensor. For example, control unit 140 may determine, based on the comparison that sensor signal dropout or early signal attenuation is detected, and thus may prompt the user to enter a reference blood glucose measurement value. In addition, certain alarm or notification functions related to the monitored analyte level such as hypoglycemic alarm, output display of glucose values in real time, may be modified or disabled given the detected anomaly with the sensor signal.

In one aspect, other variables may be compared based on the predictive model and the actual measured sensor signal such as, for example, rate of change of the glucose level determined based on the actual measured values from the sensor and compared with the modeled rate of change information. Additionally, upon determination of the sensor signal dropout or early signal attenuation condition, operations of the analyte monitoring unit 130 may be adjusted accordingly, for example, to mitigate or address the signal abnormality. For example, when such sensor signal condition indicates adverse signal condition at the time of scheduled sensor calibration, the calibration attempt may be disqualified and the user may be instructed to perform another calibration or to delay the calibration until the sensor signal has stabilized and the indicated adverse signal condition is no longer present.

Figure 12:
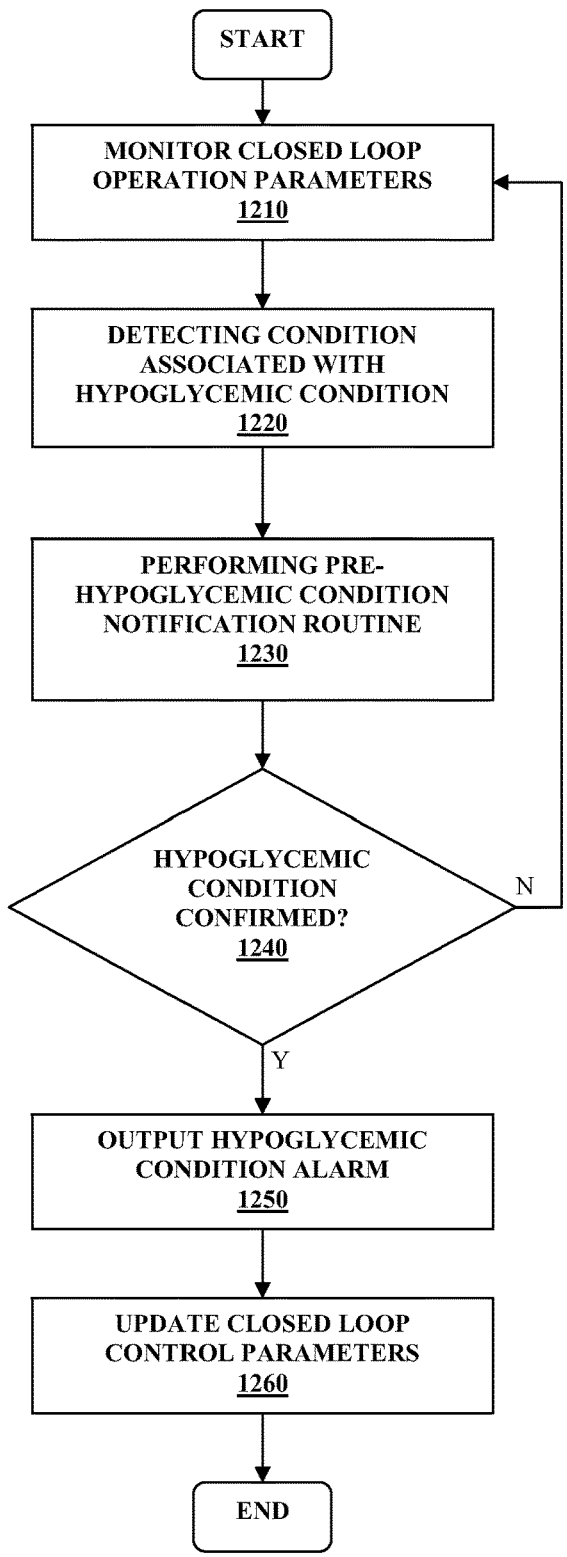
FIG. 12 is a flowchart illustrating detection of false hypoglycemic alarm condition in a closed loop control system in accordance with one embodiment of the present disclosure.

FIG. 12 is a flowchart illustrating detection of false hypoglycemic alarm condition in a closed loop control system in accordance with one embodiment of the present disclosure. Referring to FIGS. 1 and 12, in one aspect, condition associated with hypoglycemic state is detected (1220) based on monitored closed loop operation parameters (1210) by, for example, the control unit 140 (FIG. 1). Upon detection of the condition associated with the hypoglycemic state, a pre-hypoglycemic condition notification routine is performed (1230). If the hypoglycemic state or condition is confirmed (1240), then a corresponding notification such as a hypoglycemic alarm is output (1250), and the closed loop control parameters are accordingly updated to take into account of the detected hypoglycemic condition (1260).

On the other hand, if the hypoglycemic condition is not confirmed (1240), then the routine returns to monitor the closed loop operation parameters (1210). That is, in one aspect, when a condition associated with hypoglycemia is detected, the control unit 140 may be configured to confirm the presence of the detected hypoglycemic state before asserting an alarm notification, for example, to the user. In this manner, potential false hypoglycemic alarms are minimized based on, for example, presence of glucose sensor signal dropout or early signal attenuation or other sensor anomaly state that indicates a false low glucose level.

For example, in accordance with the embodiments of the present disclosure, hypoglycemic alarms or notifications are provided with sensor signal dropout tolerance levels. More specifically, based on the medication delivery rate information, and other parameters associated with the closed loop control operation, the control unit 140 may be configured to determine a degree or level of uncertainly in the measured sensor signal based on the predicted or anticipated glucose level derived, for example, based on the parameters associated with the closed loop control algorithm, including, such as amount of insulin delivered, insulin on board information, glucose rate of change information, among others.

In one aspect, when the onset of a potential hypoglycemic condition is detected, the control unit 140 may be configured to confirm the presence of the hypoglycemic condition, by for example, requiring additional sensor data to be received and analyzed and determining that the sensor signals indicate a persistent low glucose value. In this manner, rather than asserting the hypoglycemic condition notification immediately upon detection of a sensor signal level below the alarm threshold, control unit 140 in one aspect is configured to confirm the presence of the hypoglycemic condition, and upon confirmation, to assert the alarm or notification associated with the hypoglycemic condition.

In another aspect, upon detection of a potential hypoglycemic condition, control unit 140 may be configured to initiate and execute a sensor signal dropout detection algorithm to determine whether the detected potential hypoglycemic condition is associated with sensor signal dropout or attributable to low glucose level. Moreover, in a further aspect, upon detection of the potential hypoglycemic condition, control unit 140 may be configured to assert an alert notification (associated with less urgency or criticality), and if the potential hypoglycemic condition is confirmed, to assert the hypoglycemic condition alarm. For example, the alert notification may include a single audible beep that does not repeat. If the glucose is persistently below the hypoglycemic threshold (or alarm condition level), or below a lower safety threshold, the notification may be escalated to an alarm, for example, with three consecutive audible beeps with or without repeat routines. In this manner, for example, if the sensor signal dropout occurs during night time when the user is asleep, the alert notification may not be loud enough to wake the user, but may be sufficient to cause the user to move or roll over in bed, for example, resulting in the sensor dropout condition being no longer present.

In one embodiment, a method may comprise monitoring a plurality of parameters associated with a closed loop control operation including continuously monitoring a physiological condition and automatic administration of a medication, detecting an adverse condition associated with the monitored physiological condition or the medication administration deviating from a predetermined safety level of the closed loop control operation, and initiating a non-zero pre-programmed medication delivery rate.

The plurality of parameters monitored may include analyte level, insulin administration level, exercise level, analyte sensor signal condition, insulin on board information, signal transmission level, or one or more combinations thereof.

The detected adverse condition may include one or more of a failed communication state between a medication delivery device and a controller executing the closed loop control operation, absence of a valid analyte level information, or detection of medication delivery level exceeding a predetermined threshold level.

The non-zero pre-programmed medication delivery rate may include an open loop medication delivery rate.

In another embodiment, the method may further include estimating insulin on board information, and modifying the non-zero pre-programmed medication delivery rate based on the estimated insulin on board information.

In yet another embodiment, the method may further include outputting a notification based on the estimated insulin on board information.

The notification may include one or more of a recommendation to modify the medication delivery rate, or a recommendation to verify the blood glucose level.

Detecting the adverse condition may include retrieving the predetermined safety level information, confirming the presence of the detected adverse condition, and disabling the automatic medication delivery function.

Detecting the adverse condition may include determining a severity level of the detected adverse condition based on the predetermined safety level information, and generating closed loop operation instruction based on the severity level determination.

In one embodiment, a device may comprise one or more processors, and a memory operatively coupled to the one or more processors, the memory for storing instructions which, when executed by the one or more processors, causes the one or more processors to monitor a plurality of parameters associated with a closed loop control operation including continuously monitoring a physiological condition and automatic administration of a medication, detect an adverse condition associated with the monitored physiological condition or the medication administration deviating from a predetermined safety level of the closed loop control operation, and initiate a non-zero pre-programmed medication delivery rate.

The plurality of parameters monitored may include analyte level, insulin administration level, exercise level, analyte sensor signal condition, insulin on board information, signal transmission level, or one or more combinations thereof.

The detected adverse condition may include one or more of a failed communication state between a medication delivery device and a controller executing the closed loop control operation, absence of a valid analyte level information, or detection of medication delivery level exceeding a predetermined threshold level.

The non-zero pre-programmed medication delivery rate may include an open loop medication delivery rate.

The memory for storing instructions which, when executed by the one or more processors, may cause the one or more processors to estimate insulin on board information, and may modify the non-zero preprogrammed medication delivery rate based on the estimated insulin on board information.

The memory for storing instructions which, when executed by the one or more processors, may cause the one or more processors to output a notification based on the estimated insulin on board information.

The notification may include one or more of a recommendation to modify the medication delivery rate, or a recommendation to verify the blood glucose level.

The memory for storing instructions which, when executed by the one or more processors, may cause the one or more processors to retrieve the predetermined safety level information, confirm the presence of the detected adverse condition, and disable the automatic medication delivery function.

The memory for storing instructions which, when executed by the one or more processors, may cause the one or more processors to determine a severity level of the detected adverse condition based on the predetermined safety level information, and generate closed loop operation instruction based on the severity level determination.

In another embodiment, the device may include one or more of an infusion device, or an analyte monitoring device.

In yet another embodiment, the device may include a blood glucose meter.

In the manner described, in accordance with the various embodiments of the present disclosure, a robust closed loop control system is provided that includes safety checks and verifications to address potential errors and/or anomalies in detected or monitored conditions and/or parameters enhancing the accuracy and confidence level of the closed loop control operation in the treatment of diabetic conditions.

What is claimed is:

1. A method comprising:
monitoring, using one or more processors, a plurality of parameters associated with a physiological condition and an administration of a medication, including monitoring a sensor signal representative of a glucose level;
detecting a potential hypoglycemic condition associated with the physiological condition;
determining a severity level associated with the potential hypoglycemic condition, including determining a rate of change in glucose level based on previously received glucose levels stored in a memory in response to a detected communication failure from a transmitter of an analyte monitoring unit, and wherein the severity level is based at least in part on a retrieved preset safety level information;
providing a hypoglycemic alert associated with the determined severity level if the sensor signal is determined to be within a dropout tolerance level;
maintaining a medication delivery rate of the monitored administration of the medication, if the determined severity level does not exceed a preset safety level; and
initiating a fixed pre-programmed medication delivery rate when the potential hypoglycemic condition is detected if the determined severity level exceeds the preset safety level, wherein the fixed pre-programmed medication delivery rate is within a previously determined safety level and different than the medication delivery rate of the monitored administration of the medication.

2. The method of claim 1, wherein the fixed pre-programmed medication delivery rate includes an automated shut off of the administration of the medication for a predetermined time period.

3. The method of claim 2, wherein the fixed pre-programmed medication delivery rate is terminated when the glucose level exceeds a predetermined level.

4. The method of claim 1, wherein the monitored plurality of parameters further includes insulin administration level, exercise level, glucose sensor signal condition, signal transmission level, or one or more combinations thereof.

5. The method of claim 1, wherein detecting the potential hypoglycemic condition includes:
retrieving the preset safety level information;
confirming the detected potential hypoglycemic condition is a hypoglycemic condition; and
automatically disabling the administration of the medication.

6. The method of claim 1, wherein the sensor signal is provided by an in vivo analyte sensor.

7. The method of claim 6, wherein the in vivo analyte sensor comprises a plurality of electrodes including a working electrode, wherein the working electrode comprises an analyte-responsive enzyme and a mediator, wherein at least one of the analyte-responsive enzyme and the mediator is chemically bonded to a polymer disposed on the working electrode, and wherein at least one of the analyte-responsive enzyme and the mediator is crosslinked with the polymer.

8. The method of claim 1, wherein the sensor signal is determined to be within the dropout tolerance level by determining a degree of uncertainty in the sensor signal based on a predicted or anticipated glucose level.

9. The method of claim 8, wherein the medication is insulin, and the glucose level is predicted or anticipated based at least in part on a parameter associated with insulin on board information, glucose rate of change information, or amount of insulin delivered.

10. The method of claim 1, wherein detecting the potential hypoglycemic condition further comprises determining a rate of change in an analyte level, and wherein the hypoglycemic alert is further associated with the determined rate of change in the analyte level.

11. An apparatus, comprising:
one or more processors; and
a memory for storing instructions which, when executed by the one or more processors, cause the one or more processors to monitor a plurality of parameters associated with a physiological condition and an administration of a medication, including a sensor signal representative of a glucose level, to detect a potential hypoglycemic condition associated with the physiological condition, to determine a severity level associated with the potential hypoglycemic condition including determining a rate of change in glucose level based on previously received glucose levels stored in a memory in response to a detected communication failure from a transmitter of an analyte monitoring unit wherein the severity level is based at least in part on a retrieved preset safety level information, to provide a hypoglycemic alert associated with the determined severity level if the sensor signal is determined to be within a dropout tolerance level, to maintain a medication delivery rate of the monitored administration of the medication if the determined severity level does not exceed a preset safety level, and to initiate a fixed pre-programmed medication delivery rate when the adverse condition is detected if the determined severity level exceeds a preset safety level, wherein the fixed pre-programmed medication delivery rate is within a previously determined safety level and different than the medication delivery rate of the monitored administration of medication.

12. The apparatus of claim 11, wherein the fixed preprogrammed medication delivery rate includes an automated shut off of the administration of the medication for a predetermined time period.

13. The apparatus of claim 12, wherein the fixed preprogrammed medication delivery rate is terminated when the monitored glucose level exceeds a predetermined level.

14. The apparatus of claim 11, wherein the monitored plurality of parameters further includes insulin administration level, exercise level, glucose sensor signal condition, signal transmission level, or one or more combinations thereof.

15. The apparatus of claim 11, wherein the instructions, when executed by the one or more processors, cause the one or more processors to retrieve the preset safety level information, confirm the detected potential hypoglycemic condition as a hypoglycemic condition, and automatically disable the administration of medication.

16. The apparatus of claim 11, further comprising an in vivo analyte sensor.

17. The apparatus of claim 16, wherein the in vivo analyte sensor comprises a plurality of electrodes including a working electrode, wherein the working electrode comprises an analyte-responsive enzyme and a mediator, wherein at least one of the analyte-responsive enzyme and the mediator is chemically bonded to a polymer disposed on the working electrode, and wherein at least one of the analyte-responsive enzyme and the mediator is crosslinked with the polymer.

18. The apparatus of claim 11, wherein the sensor signal is determined to be within the dropout tolerance level by using a predicted or anticipated glucose level to determine a degree of uncertainty in the sensor signal.

19. The apparatus of claim 18, wherein the medication is insulin, and the glucose level is predicted or anticipated based at least in part on a parameter associated with insulin on board information, glucose rate of change information, or amount of insulin delivered.

\* \* \* \* \*